United States Patent
Nakamura et al.

(10) Patent No.: US 11,295,442 B2
(45) Date of Patent: Apr. 5, 2022

(54) MEDICAL INFORMATION DISPLAY APPARATUS DISPLAYING CAVITY REGION IN BRAIN IMAGE, MEDICAL INFORMATION DISPLAY METHOD, AND MEDICAL INFORMATION DISPLAY PROGRAM

(71) Applicant: FUJIFILM Corporation, Tokyo (JP)

(72) Inventors: Keigo Nakamura, Tokyo (JP); Caihua Wang, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 159 days.

(21) Appl. No.: 16/792,325

(22) Filed: Feb. 17, 2020

(65) Prior Publication Data

US 2020/0202526 A1 Jun. 25, 2020

Related U.S. Application Data

(63) Continuation of application No. PCT/JP2018/021210, filed on Jun. 1, 2018.

(30) Foreign Application Priority Data

Aug. 29, 2017 (JP) .............................. JP2017-164672

(51) Int. Cl.
*G06T 7/38* (2017.01)
*G06T 7/00* (2017.01)
(Continued)

(52) U.S. Cl.
CPC .......... *G06T 7/0012* (2013.01); *A61B 5/0042* (2013.01); *A61B 5/4064* (2013.01);
(Continued)

(58) Field of Classification Search
CPC ..................... G06T 7/0012; G06T 7/38; G06T 2207/10081; G06T 2207/10088;
(Continued)

(56) References Cited

U.S. PATENT DOCUMENTS 8,160,676 B2 * 4/2012 Gielen ................ A61B 6/5247
600/427
2009/0292551 A1 11/2009 Sirohey et al.
(Continued)

FOREIGN PATENT DOCUMENTS

EP 3199102 8/2017
JP 2011010828 1/2011
(Continued)

OTHER PUBLICATIONS

Colin Studholme, et al., "Deformation-Based Mapping of Volume Change From Serial Brain MRI in the Presence of Local Tissue Contrast Change", IEEE Transactions on Medical Imaging, vol. 25, No. 5, May 2006, pp. 626-639.
(Continued)

*Primary Examiner* — Siamak Harandi
(74) *Attorney, Agent, or Firm* — JCIPRNET

(57) ABSTRACT

The medical information display apparatus includes an image acquisition unit that acquires a first brain image which is a brain image of a subject captured at a first time point and a second brain image captured at a second time point later in time than the first time point, a registration unit that performs registration between the first and the second brain image, an image analysis unit that extracts a first cavity region and a second cavity region from the first brain image and the second brain image, respectively, a display unit, and a display controller displays, a cavity expansion part included in a first non-cavity region, which is a region other than the first cavity region, and included in the second cavity region in a distinguishable manner from a region other than the cavity expansion part from a result of the registration between the first and second brain image.

20 Claims, 23 Drawing Sheets

(51) Int. Cl.
  *G16H 10/60* (2018.01)
  *A61B 5/00* (2006.01)
  *G06V 10/40* (2022.01)

(52) U.S. Cl.
  CPC .......... *A61B 5/4088* (2013.01); *A61B 5/4842* (2013.01); *A61B 5/7425* (2013.01); *G06T 7/0016* (2013.01); *G06T 7/38* (2017.01); *G06V 10/40* (2022.01); *G16H 10/60* (2018.01); *G06T 2207/10081* (2013.01); *G06T 2207/10088* (2013.01); *G06T 2207/10104* (2013.01); *G06T 2207/10108* (2013.01); *G06T 2207/20021* (2013.01); *G06T 2207/30016* (2013.01)

(58) Field of Classification Search
  CPC . G06T 2207/10104; G06T 2207/10108; G06T 2207/20021; G06T 2207/30016; G06T 2200/24; G06T 2207/10072; G06T 2207/20092; G06T 2207/20128; G06T 7/344; G06T 7/0016; G16H 10/60; G06K 9/46; A61B 6/037; A61B 6/032; A61B 5/748; A61B 5/7425; A61B 5/4088; A61B 5/4842; A61B 5/4064; A61B 5/0042; A61B 5/055
  See application file for complete search history.

(56) References Cited

U.S. PATENT DOCUMENTS

| | | |
|---|---|---|
| 2017/0024888 A1 | 1/2017 | Ishii et al. |
| 2020/0315455 A1 | 10/2020 | Lee et al. |

FOREIGN PATENT DOCUMENTS

| | | |
|---|---|---|
| JP | 2014042684 | 3/2014 |
| JP | 2017023457 | 2/2017 |
| KR | 101754291 | 7/2017 |
| WO | 02101407 | 12/2002 |
| WO | 2012032940 | 3/2012 |

OTHER PUBLICATIONS

Paul M. Thompson, et al., "Tracking Alzheimer's Disease", Annals of the New York Academy of Sciences, Feb. 2007, pp. 1-28.

Valerie Anderson, "Assessment and optimisation of MRI measures of atrophy as potential markers of disease progression in multiple sclerosis", Thesis submitted for the degree of Doctor of Philosophy, University of Auckland, Jan. 1, 2008, pp. 1-288.

"Search Report of Europe Counterpart Application", dated Sep. 10, 2020, pp. 1-13.

Dominic Holland, et al., "Subregional neuroanatomical change as a biomarker for Alzheimer's disease." Proceedings of the National Academy of Sciences, vol. 106, No. 49, Dec. 8, 2009, pp. 20954-20959.

Yakang Dai, et al., "aBEAT: A Toolbox for Consistent Analysis of Longitudinal Adult Brain MRI." PLOS One, vol. 8, No. 4, Apr. 3, 2013, pp. 1-13.

International Search Report (Form PCT/ISA/210) of PCT/JP2018/021210, dated Jul. 24, 2018, with English translation thereof, pp. 1-3.

"Written Opinion of the International Searching Authority (Form PCT/ISA/237)" of PCT/JP2018/021210, dated Jul. 24, 2018, with English translation thereof, pp. 1-7.

* cited by examiner

FIG. 6

| NUMBER | DESCRIPTION OF NAME OF BRAIN AREA |
|---|---|
| 1, 2, 3 | POSTERIOR CENTRAL CONVOLUTION OR PRIMARY SOMATOSENSORY CORTEX |
| 4 | ANTERIOR CENTRAL CONVOLUTION OR PRIMARY MOTOR CORTEX |
| 5 | SOMATOSENSORY ASSOCIATION CORTEX |
| 6 | PREMOTOR CORTEX AND SUPPLEMENTARY MOTOR AREA |
| 7 | SOMATOSENSORY ASSOCIATION CORTEX |
| 8 | FRONTAL EYE FIELD |
| 9 | DORSOLATERAL PREFRONTAL CORTEX |
| 10 | FRONTAL POLE |
| 11 | ORBITOFRONTAL CORTEX |
| 12 | ORBITOFRONTAL CORTEX |
| 13 | INSULAR CORTEX |
| 17 | PRIMARY VISUAL CORTEX (V1) |
| 18 | SECONDARY VISUAL CORTEX (V2) |
| 19 | ASSOCIATIVE VISUAL CORTEX (V3) |
| 20 | INFERIOR TEMPORAL GYRUS |
| 21 | MIDDLE TEMPORAL GYRUS |
| 22 | SUPERIOR TEMPORAL GYRUS |
| 23 | VENTRAL POSTERIOR CINGULATE CORTEX |
| 24 | VENTRAL ANTERIOR CINGULATE CORTEX |
| 25 | SUBGENUAL CORTEX |
| 26 | Ectosplenial area |
| 27 | PIRIFORM CORTEX |
| 28 | VENTRAL ENTORHINAL CORTEX |
| 29 | RETROSPLENIAL CINGULATE CORTEX |
| 30 | PART OF CINGULATE CORTEX |
| 31 | DORSAL POSTERIOR CINGULATE CORTEX |
| 32 | DORSAL ANTERIOR CINGULATE CORTEX |
| 33 | PART OF ANTERIOR CINGULATE CORTEX |
| 34 | DORSAL ENTORHINAL CORTEX (on the PARAHIPPOCAMPAL GYRUS) |
| 35 | PERIRHINAL CORTEX (on the PARAHIPPOCAMPAL GYRUS) |
| 36 | PARAHIPPOCAMPAL CORTEX (on the PARAHIPPOCAMPAL GYRUS) |
| 37 | FUSIFORM GYRUS |
| 38 | TEMPORAL POLE |
| 39 | ANGULAR GYRUS |
| 40 | SUPRAMARGINAL GYRUS |
| 41 | PRIMARY AUDITORY CORTEX |
| 42 | PRIMARY AUDITORY CORTEX |
| 43 | PRIMARY GUSTATORY CORTEX |
| 44 | INFERIOR FRONTAL GYRUS PARS OPERCULARIS |
| 45 | INFERIOR FRONTAL GYRUS PARS TRIANGULARIS |
| 46 | DORSOLATERAL PREFRONTAL CORTEX |
| 47 | PARS ORBITALIS |
| 48 | RETROSUBICULAR AREA |
| 52 | PARAINSULAR AREA |

FIG. 9

| | ITEM | POINT |
|---|---|---|
| 1 | WORD REPRODUCIBILITY | 4/10 |
| 2 | SPOKEN LANGUAGE | 3/5 |
| 3 | AUDITORY COMPREHENSION OF LANGUAGE | 2/5 |
| 4 | DIFFICULTY IN SPEAKING IN SPONTANEOUS SPEECH | 4/5 |
| 5 | ACCORDING TO VERBAL COMMAND | 3/5 |
| 6 | FINGER AND ARTICLE DESIGNATION | 2/5 |
| 7 | CONSTRUCTIVE ACTION (DRAWING) | 3/5 |
| 8 | IDEA MOVEMENT | 1/5 |
| 9 | ORIENTATION | 4/8 |
| 10 | WORD RECOGNITION | 8/12 |
| 11 | TEST TEACHING REPRODUCIBILITY | 2/5 |
| | TOTAL | 35/70 |

| COORDINATE (x, y, z) | BRAI AREA LABEL (NAME) |
|---|---|
| (0, 0, 0) | OUTSIDE BRAIN |
| ⋮ | ⋮ |
| (45, 50, 77) | DORSOLATERAL PREFRONTAL CORTEX (9) |
| ⋮ | ⋮ |
| (77, 91, 110) | ORBITOFRONTAL CORTEX (11) |
| ⋮ | ⋮ |

FIG. 16

| BRAIN AREA NUMBER \ ELEVEN ITEMS OF ADAS | 1 | 2 | ..... | 11 |
|---|---|---|---|---|
| 1 | RELEVANCE $A_{1,1}$ |  | ..... | $A_{1,11}$ |
| ⋮ | ⋮ | ⋮ | ..... | ⋮ |
| 20 | RELEVANCE $A_{20,1}$ = 0.45 | $A_{20,2}$ | ..... | $A_{20,11}$ |
| 21 | $A_{21,1}$ | $A_{21,2}$ | ..... | $A_{21,11}$ |
| 22 | RELEVANCE $A_{22,1}$ = 0.30 | $A_{22,2}$ | ..... | $A_{22,11}$ |
| ⋮ | ⋮ | ⋮ | ..... | ⋮ |
| 52 | $A_{52,1}$ | $A_{52,2}$ | ..... | $A_{52,11}$ |

T1

| No. | NAME OF BRAIN AREA | FUNCTION | ATROPHY RATE |
|---|---|---|---|
| 001 | .... | .... | % |
| 002 | .... | .... | % |
| 003 | .... | .... | % |
| ⋮ | ⋮ | ⋮ | ⋮ |

FIG. 25

| NUMBER | DESCRIPTION OF NAME OF BRAIN AREA | FUNCTION | POSITION | ANALYSIS VALUE |
|---|---|---|---|---|
| 1, 2, 3 | POSTERIOR CENTRAL CONVOLUTION OR PRIMARY SOMATOSENSORY CORTEX | PRIMARY CENTER OF TACTILE SENSATION, DEEP SENSATION, AND PAIN AND TEMPERATURE SENSATION | | |
| 4 | ANTERIOR CENTRAL CONVOLUTION OR PRIMARY MOTOR CORTEX | MOVEMENT OF UPPER LIMBS, LOWER LIMBS, FACE, AND TONGUE | | |
| 5 | SOMATOSENSORY ASSOCIATION CORTEX | ⋮ | | |
| 6 | PREMOTOR CORTEX AND SUPPLEMENTARY MOTOR AREA | ADJUSTMENT OF SKELETAL MUSCLE MOVEMENT | | |
| 7 | SOMATOSENSORY ASSOCIATION CORTEX | | | |
| 8 | FRONTAL EYE FIELD | ⋮ | | |
| 9 | DORSOLATERAL PREFRONTAL CORTEX | | | |
| 10 | FRONTAL POLE | INTELLIGENCE AND EMOTION | | |
| 11 | ORBITOFRONTAL CORTEX | | | |
| 12 | ORBITOFRONTAL CORTEX | ⋮ | | |
| 13 | INSULAR CORTEX | | | |
| 17 | PRIMARY VISUAL CORTEX (V1) | PRIMARY VISUAL CENTER | | |
| 18 | SECONDARY VISUAL CORTEX (V2) | SECONDARY VISUAL CENTER | | |
| 19 | ASSOCIATIVE VISUAL CORTEX (V3) | | | |
| 20 | INFERIOR TEMPORAL GYRUS | SENSORY STIMULATION INTEGRATION, AUDITORY LANGUAGE, AND MEMORY | | |
| 21 | MIDDLE TEMPORAL GYRUS | | | |
| 22 | SUPERIOR TEMPORAL GYRUS | SECONDARY AUDITORY CENTER | | |
| 23 | VENTRAL POSTERIOR CINGULATE CORTEX | STORAGE AND RETRIEVAL OF MEMORY OLFACTORY CENTER | | |
| 24 | VENTRAL ANTERIOR CINGULATE CORTEX | | | |
| 25 | SUBGENUAL CORTEX | | | |
| 26 | Ectosplenial area | | | |
| 27 | PIRIFORM CORTEX | | | |
| 28 | VENTRAL ENTORHINAL CORTEX | | | |
| 29 | RETROSPLENIAL CINGULATE CORTEX | | | |
| 30 | PART OF CINGULATE CORTEX | | | |
| 31 | DORSAL POSTERIOR CINGULATE CORTEX | | | |
| 32 | DORSAL ANTERIOR CINGULATE CORTEX | | | |
| 33 | PART OF ANTERIOR CINGULATE CORTEX | | | |
| 34 | DORSAL ENTORHINAL CORTEX (on the PARAHIPPOCAMPAL GYRUS) | | | |
| 35 | PERIRHINAL CORTEX (on the PARAHIPPOCAMPAL GYRUS) | | | |
| 36 | PARAHIPPOCAMPAL CORTEX (on the PARAHIPPOCAMPAL GYRUS) | ⋮ | | |
| 37 | FUSIFORM GYRUS | | | |
| 38 | TEMPORAL POLE | | | |
| 39 | ANGULAR GYRUS | | | |
| 40 | SUPRAMARGINAL GYRUS | | | |
| 41 | PRIMARY AUDITORY CORTEX | PRIMARY AUDITORY CENTER | | |
| 42 | PRIMARY AUDITORY CORTEX | SECONDARY AUDITORY CENTER | | |
| 43 | PRIMARY GUSTATORY CORTEX | PRIMARY GUSTATORY CENTER | | |
| 44 | INFERIOR FRONTAL GYRUS PARS OPERCULARIS | EXPRESS LANGUAGE (WRITE AND SPEAK) | | |
| 45 | INFERIOR FRONTAL GYRUS PARS TRIANGULARIS | | | |
| 46 | DORSOLATERAL PREFRONTAL CORTEX | ⋮ | | |
| 47 | PARS ORBITALIS | | | |
| 48 | RETROSUBICULAR AREA | | | |
| 52 | PARAINSULAR AREA | | | |

T10

MEDICAL INFORMATION DISPLAY APPARATUS DISPLAYING CAVITY REGION IN BRAIN IMAGE, MEDICAL INFORMATION DISPLAY METHOD, AND MEDICAL INFORMATION DISPLAY PROGRAM

CROSS REFERENCE TO RELATED APPLICATIONS

This application is a Continuation of PCT International Application No. PCT/JP2018/021210 filed on Jun. 1, 2018, which claims priority under 35 U.S.C § 119(a) to Patent Application No. 2017-164672 filed in Japan on Aug. 29, 2017, all of which are hereby expressly incorporated by reference into the present application.

BACKGROUND OF THE INVENTION

1. Field of the Invention

The present invention relates to a medical information display apparatus, a medical information display method, and a non-transitory computer readable recording medium storing a medical information display program, and particularly relates to a medical information display apparatus, a medical information display method, and a non-transitory computer readable recording medium storing a medical information display program for supporting diagnosis of dementia for a subject (patient) by a doctor or the like.

2. Description of the Related Art

With the arrival of an aging society, the number of patients with dementia is increasing year by year. It is considered that dementia develops in a case where a protein called amyloid 3 accumulates in the brain and accordingly brain atrophy progresses and cognitive ability declines. At present, there is no effective treatment for dementia. For this reason, it is important in terms of maintaining the quality of life to detect brain atrophy early and start treatment early to delay the progression of dementia.

In order to meet such a demand, in recent years, information regarding the state of the brain can be acquired by nuclear medicine examinations such as single photon emission computed tomography (SPECT) and positron emission tomography (PET), CT images acquired by computerized tomography (CT) apparatuses, and MRI images acquired by magnetic resonance imaging (MRI) apparatuses. For example, decreased blood flow and metabolism in a local part of the brain can be found by checking a temporal change in the local part of the brain using SPECT and PET images.

On the other hand, brain atrophy can be found by calculating the volume of a specific part of the brain using MRI images and comparing a temporal change in the volume. For example, in JP2014-042684A, a method of performing registration of two brain images having different imaging dates and times, and then dividing each of the two brain images into tissue regions (gray matter and white matter) to acquire the change amount for each tissue region has been proposed.

On the other hand, for example, a method of performing registration between a standard brain image divided according to a Broadmann's brain map and a brain image of a patient and dividing the brain image of the patient into regions has been proposed (see JP2011-010828A). Here, the Broadmann's brain map shows that which region carries out certain brain function (movement, language, perception, memory, vision sense, acoustic sense, and the like) within a three-dimensional region of the cerebral cortex of the standard brain. Thus, a method of dividing the brain image of the patient into regions and acquiring the change amount in the volume for each region has been proposed (Dominic Holland, et al., Alzheimer's Disease Neuroimaging Initiative, "Subregional neuroanatomical change as a biomarker for Alzheimer's disease", Proceedings of the National Academy of Sciences, National Academy of Sciences, Dec. 8, 2009, vol. 106, no. 49, pp. 20954 to 20959 and Yakang Dai, et al., Alzheimer's Disease Neuroimaging Initiative, "aBEAT: A Toolbox for Consistent Analysis of Longitudinal Adult Brain MRI", PLoS ONE, Public Library of Science, Apr. 3, 2013, vol. 8, issue 4). In the method disclosed in Dominic Holland, et al., Alzheimer's Disease Neuroimaging Initiative, "Subregional neuroanatomical change as a biomarker for Alzheimer's disease", Proceedings of the National Academy of Sciences, National Academy of Sciences, Dec. 8, 2009, vol. 106, no. 49, pp. 20954 to 20959 and Yakang Dai, et al., Alzheimer's Disease Neuroimaging Initiative, "aBEAT: A Toolbox for Consistent Analysis of Longitudinal Adult Brain MRI", PLoS ONE, Public Library of Science, Apr. 3, 2013, vol. 8, issue 4, first, a first brain image of the patient and a standard brain image are registered to divide the first brain image into regions, and a second brain image of the patient whose imaging date and time is later than that of the first brain image and a standard brain image are registered to divide the second brain image into regions. Then, the change amount in the volume is acquired between corresponding regions in the first brain image and the second brain image.

SUMMARY OF THE INVENTION

However, even though an analysis value such as an atrophy rate is calculated as a numerical value for each region divided into a number of regions, it is difficult for a doctor or the like to determine dementia based on the numerical value for each region.

The present invention has been made in view of such circumstances, and it is an object of the present invention to provide a medical information display apparatus, a medical information display method, and a medical information display program capable of appropriately displaying an atrophy state of the brain in order to support a doctor's diagnosis of dementia.

A medical information display apparatus according to a first aspect of the present invention comprises: an image acquisition unit that acquires a first brain image which is a brain image of a subject captured at a first time point and a second brain image which is a brain image of the subject captured at a second time point later in time than the first time point; a registration unit that performs registration between the first brain image and the second brain image; an image analysis unit that extracts a first cavity region and a second cavity region from the first brain image and the second brain image, respectively; a display unit; and a display controller that displays, on the display unit, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image.

According to the first aspect, in the medical information display apparatus according to a second aspect of the present invention, the display controller is configured to display, on the display unit, a cavity contraction part included in the first cavity region in the first brain image and included in a second non-cavity region which is a region other than the second cavity region in the second brain image in a distinguishable manner from a region other than the cavity contraction part.

A medical information display apparatus according to a third aspect of the present invention comprises: an image acquisition unit that acquires a first brain image which is a brain image of a subject captured at a first time point and a second brain image which is a brain image of the subject captured at a second time point later in time than the first time point; a registration unit that performs registration between the first brain image and the second brain image; an image analysis unit that extracts a first cavity region and a second cavity region from the first brain image and the second brain image, respectively; a display unit; and a display controller that displays, on the display unit, a cavity contraction part included in the first cavity region in the first brain image and included in a second non-cavity region which is a region other than the second cavity region in the second brain image in a distinguishable manner from a region other than the cavity contraction part from a result of the registration between the first brain image and the second brain image.

According to any one of the first to third aspects, in the medical information display apparatus according to a fourth aspect of the present invention, the display controller is configured to display, on the display unit, a cavity part that is a region commonly included in both the first cavity region and the second cavity region in a distinguishable manner from a region other than the cavity part.

According to any one of the first to fourth aspects, in the medical information display apparatus according to a fifth aspect of the present invention, the display controller is configured to display, on the display unit, a non-cavity part that is a region commonly included in both the first non-cavity region which is a region other than the first cavity region in the first brain image and a second non-cavity region which is a region other than the second cavity region in the second brain image in a distinguishable manner from a region other than the non-cavity part.

According to any one of the first to fifth aspects, the medical information display apparatus according to a sixth aspect of the present invention further comprises: a brain area division unit that divides at least one of the first brain image or the second brain image into a plurality of brain areas, in which the image analysis unit is configured to calculate a change of each brain area due to a change of the cavity region in the first brain image and the second brain image, and the display controller is configured to display the change of each brain area on the display unit.

According to the sixth aspect, in the medical information display apparatus according to a seventh aspect of the present invention, the image analysis unit is configured to calculate at least one of a size change or a shape change of each brain area due to the change of the cavity region in the first brain image and the second brain image.

According to the sixth or seventh aspect, the medical information display apparatus according to an eighth aspect of the present invention further comprises: a first data acquisition unit that acquires information indicating correspondence between the brain area and a brain function, in which the display controller is configured to display information on the brain function corresponding to each brain area on the display unit.

According to any one of the sixth to eighth aspects, the medical information display apparatus according to a ninth aspect of the present invention further comprises: a second data acquisition unit that acquires a table showing relevance between at least one item included in clinical diagnostic information on dementia and the brain area, in which the display controller is configured to specify at least one item included in the clinical diagnostic information corresponding to each brain area and display the specified item on the display unit based on the table.

A medical information display method according to a tenth aspect of the present invention comprises: an image acquisition step of acquiring a first brain image which is a brain image of a subject captured at a first time point and a second brain image which is a brain image of the subject captured at a second time point later in time than the first time point; a registration step of performing registration between the first brain image and the second brain image; an image analysis step of extracting a first cavity region and a second cavity region from the first brain image and the second brain image, respectively; and a display control step of displaying, on the display unit, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image.

A medical information display method according to an eleventh aspect of the present invention comprises: an image acquisition step of acquiring a first brain image which is a brain image of a subject captured at a first time point and a second brain image which is a brain image of the subject captured at a second time point later in time than the first time point; a registration step of performing registration between the first brain image and the second brain image; an image analysis step of extracting a first cavity region and a second cavity region from the first brain image and the second brain image, respectively; and a display control step of displaying, on a display unit, a cavity contraction part included in the first cavity region in the first brain image and included in a second non-cavity region which is a region other than the second cavity region in the second brain image in a distinguishable manner from a region other than the cavity contraction part from a result of the registration between the first brain image and the second brain image.

A medical information display program according to a twelfth aspect of the present invention for causing a computer to realize: an image acquisition function of acquiring a first brain image which is a brain image of a subject captured at a first time point and a second brain image which is a brain image of the subject captured at a second time point later in time than the first time point; a registration function of performing registration between the first brain image and the second brain image; an image analysis function of extracting a first cavity region and a second cavity region from the first brain image and the second brain image, respectively; and a display control function of displaying, on the display unit, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image.

A medical information display program according to a thirteenth aspect of the present invention for causing a computer to realize: an image acquisition function of acquiring a first brain image which is a brain image of a subject captured at a first time point and a second brain image which is a brain image of the subject captured at a second time point later in time than the first time point; a registration function of performing registration between the first brain image and the second brain image; an image analysis function of extracting a first cavity region and a second cavity region from the first brain image and the second brain image, respectively; and a display control function of displaying, on a display unit, a cavity contraction part included in the first cavity region in the first brain image and included in a second non-cavity region which is a region other than the second cavity region in the second brain image in a distinguishable manner from a region other than the cavity contraction part from a result of the registration between the first brain image and the second brain image. In addition, the medical information display apparatus according to another aspect of the present invention comprises: a memory for storing an instruction for causing a computer to execute processing; and a processor configured to execute the stored instruction, in which the processor acquires a first brain image which is a brain image of a subject captured at a first time point and a second brain image which is a brain image of the subject captured at a second time point later in time than the first time point, performs registration between the first brain image and the second brain image, extracts a first cavity region and a second cavity region from the first brain image and the second brain image, respectively, and displays, on the display unit, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image.

According to the present invention, it is possible to support a doctor's diagnosis of dementia by displaying an atrophy state of the brain easily and appropriately for the doctor.

BRIEF DESCRIPTION OF THE DRAWINGS

FIG. 6 is a diagram showing a table T3 including numbers indicating brain areas and names of the respective brain areas.

FIG. 9 is a diagram showing diagnostic data indicating ADAS test results.

FIG. 10 is a diagram illustrating the association between three-dimensional information of all voxels forming a brain image and brain area labels.

FIG. 16 is a diagram schematically showing a first table.

FIG. 25 is a diagram showing an example of an analysis result table.

DESCRIPTION OF THE PREFERRED EMBODIMENTS

Hereinafter, embodiments of a medical information display apparatus, a medical information display method, and a medical information display program according to the present invention will be described with reference to the accompanying diagrams.

<Apparatus Configuration>

Figure 1:
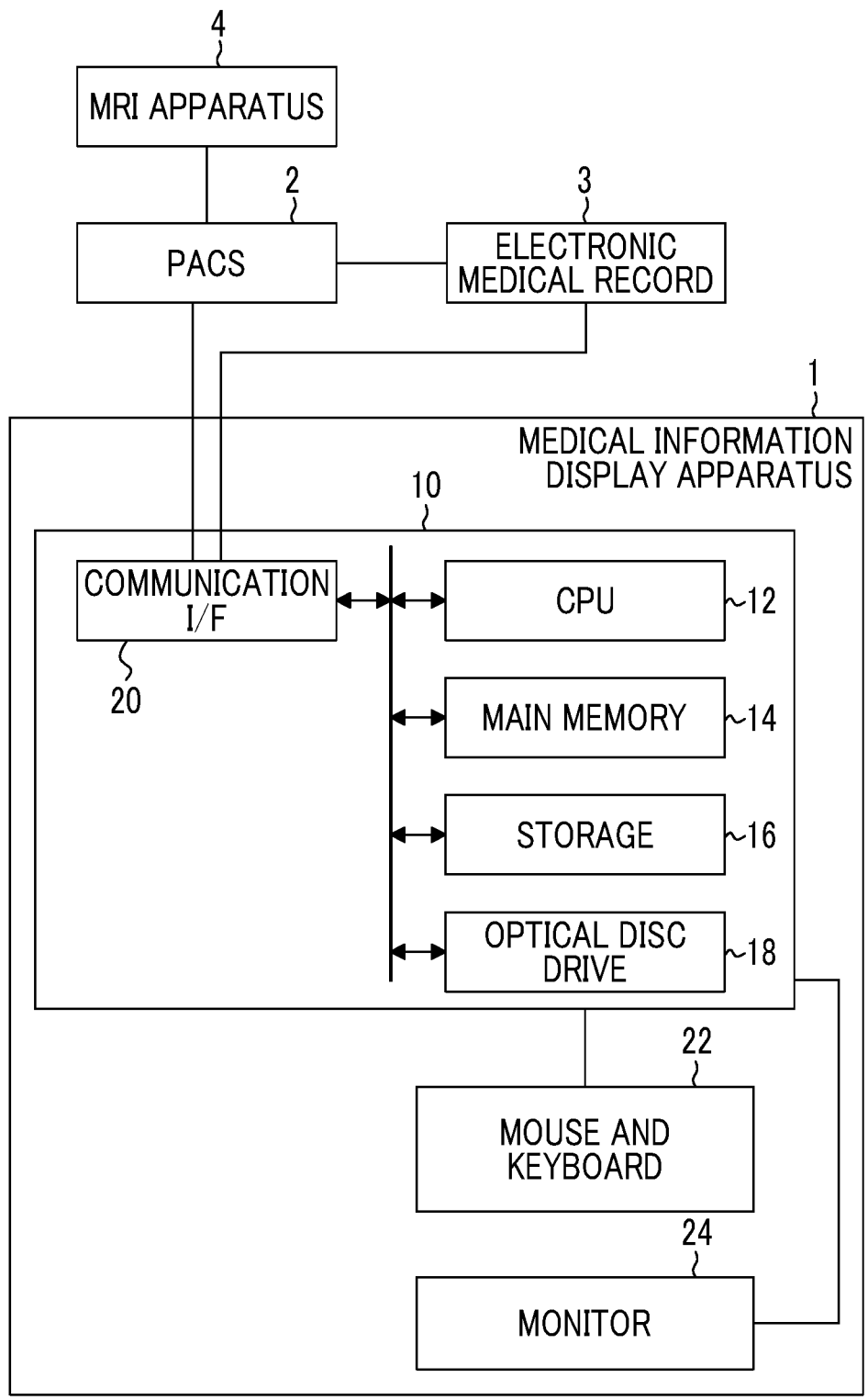
FIG. 1 is a hardware configuration diagram showing the outline of a system including a medical information display apparatus according to the present invention.

FIG. 1 is a hardware configuration diagram showing the outline of a system including a medical information display apparatus according to the embodiment of the present invention.

The system shown in FIG. 1 is configured to include a medical information display apparatus 1, picture archiving and communication systems (PACS) 2, an electronic medical record 3, and a magnetic resonance imaging (MRI) apparatus 4.

The MRI apparatus 4 continuously measures nuclear magnetic resonance signals from hydrogen, phosphorus, and the like in a subject and visualizes the nuclear density distribution, relaxation time distribution, and the like, and is an apparatus that acquires a three-dimensional image showing a part as a diagnostic target of a patient who is the subject. As an apparatus for acquiring a three-dimensional image of a subject, there is a CT apparatus capable of acquiring a computed tomography (CT) image in addition to the MRI apparatus 4.

In the present invention, a diagnostic target part of a patient who is a subject is a brain, and the MRI apparatus 4 outputs an MRI image of the head including the brain of the subject as a three-dimensional brain image.

The three-dimensional brain image is configured as a set of axial tomographic images (slice images) according to a predetermined slice interval or slice thickness (for example, a group of several hundred images). A voxel in each slice image corresponds to a pixel of a two-dimensional image having a slice thickness, and each voxel has three-dimensional information.

The PACS 2 is a unit that centrally manages digital medical image information, which is obtained from a plurality of examination apparatuses (modalities), as electronic data. A three-dimensional brain image captured by the MRI apparatus 4 that is one of the modalities is stored and managed by the PACS 2 and used for searching, browsing, and the like by the electronic medical record 3 or the medical information display apparatus 1.

In the PACS 2, image storage and communication are performed using the image format and communication protocol of digital imaging and communication in medicine (DICOM). In the image format of the DICOM standard, parameters, diagnostic information, and the like at the time of imaging can be stored in the header portion of the file. In the present embodiment, it is assumed that a plurality of three-dimensional brain images having different imaging dates and times for the same subject are stored and managed in the PACS 2.

The medical information display apparatus 1 is obtained by installing an information output program according to the embodiment of the present invention on one computer 10, and the computer may be a workstation or a personal computer that is directly operated by the doctor who performs diagnosis or may be a server computer connected to these through a network.

The information output program is distributed in a state in which the information output program is recorded on an optical disc (recording medium), such as a digital versatile disc (DVD) or a compact disc read only memory (CD-ROM), and is installed from the optical disc onto the computer 10 through an optical disc drive 18.

An operation unit 22, such as a mouse and a keyboard that function as an operation unit, and a monitor (display unit) 24 are connected to the computer 10. Here, the monitor 24 of FIG. 1 may be a liquid crystal monitor, or may be provided with a head mounted display instead of or in addition to the liquid crystal monitor.

The computer 10 is configured to mainly include: a central processing unit (CPU) 12 that perform overall control of the operation of each component; a main memory 14 that stores an apparatus control program or serves as a working area at the time of executing the program; a storage 16 such as a hard disk apparatus; the optical disc drive 18 for reading and writing various kinds of data and programs recorded on the optical disc; and a communication interface (communication I/F) 20 for exchanging necessary information with the PACS 2, the electronic medical record 3, and the like.

In addition to various kinds of application software including a medical information display program according to the embodiment of the present invention, a reference brain image, and various tables (will be described later) used in the present invention, brain images of the subject acquired from the PACS 2 through the communication I/F 20 and various kinds of information including diagnostic information acquired from the electronic medical record 3 are stored in the storage 16. The diagnostic information includes data indicating the test results of alzheimers' disease assessment scale (ADAS) or alzheimer's disease assessment scale Japanese version (ADAS-Jcog).

Figure 2:
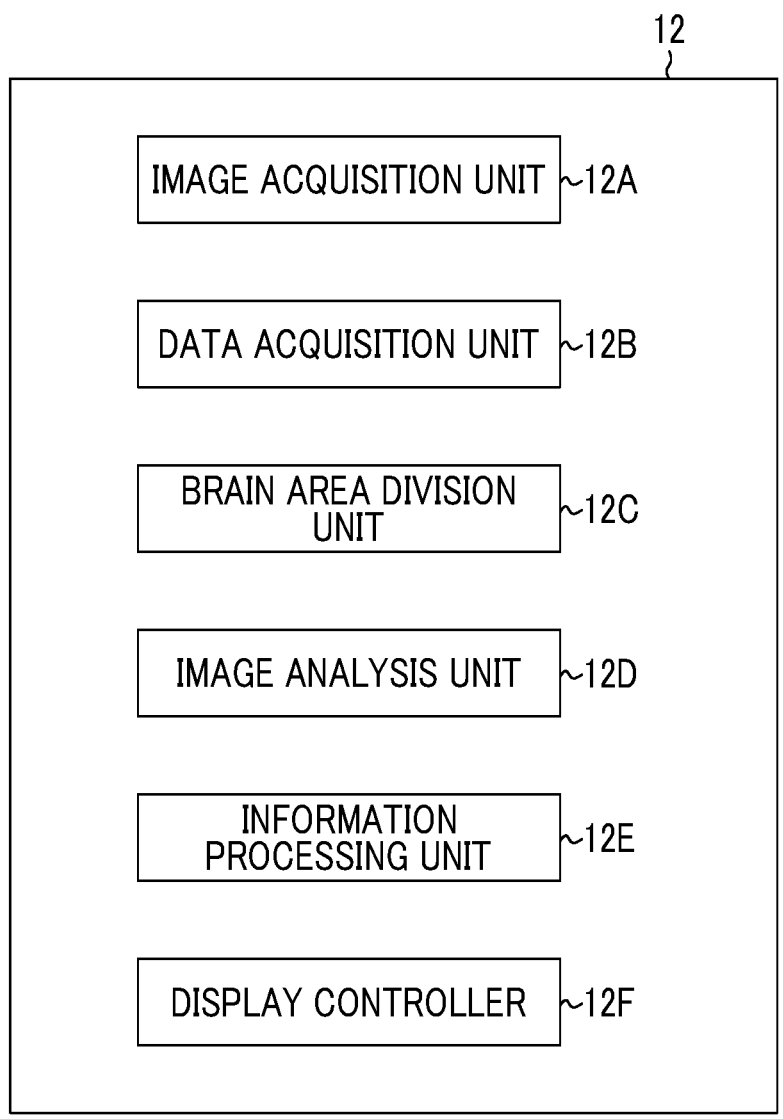
FIG. 2 is a functional block diagram showing a function of a CPU of the medical information display apparatus shown in FIG. 1.

FIG. 2 is a functional block diagram showing a function of a CPU 12 of the medical information display apparatus 1 shown in FIG. 1.

The CPU 12 functions as various processing units by executing the medical information display program stored in the storage 16. In this embodiment, the CPU 12 has functions as an image acquisition unit 12A, a data acquisition unit 12B, a brain area division unit 12C, an image analysis unit 12D, an information processing unit 12E, and a display controller 12F.

The image acquisition unit 12A acquires a three-dimensional standard brain image Bs and a three-dimensional first brain image B1 and a three-dimensional second brain image B2 including the brain of the same subject and having different imaging dates and times.

The standard brain image Bs is a three-dimensional brain image showing a brain having a standard shape and size and a standard density (pixel value), that is, a standard brain. The standard brain image Bs can be generated by extracting brains from a plurality of brain images, which are acquired by imaging the heads of a plurality of healthy persons with a three-dimensional image capturing apparatus, and averaging the plurality of extracted brains.

The standard brain image Bs includes division information for dividing the entire brain into a plurality of brain areas. As a method of division, for example, based on the Broadmann's brain map, within the three-dimensional region of the cerebral cortex, it is possible to use a method of dividing the cerebral cortex into brain areas responsible for functions, such as movement, language, perception, memory, vision sense, and acoustic sense. In addition, it is possible to use any known method, such as a method for division into six kinds of brain areas of cerebrum, diencephalon, mesencephalon, hindbrain, cerebellum, and medulla oblongata and a method of dividing the cerebrum into frontal lobe, parietal lobe, temporal lobe, and occipital lobe.

Figure 3:
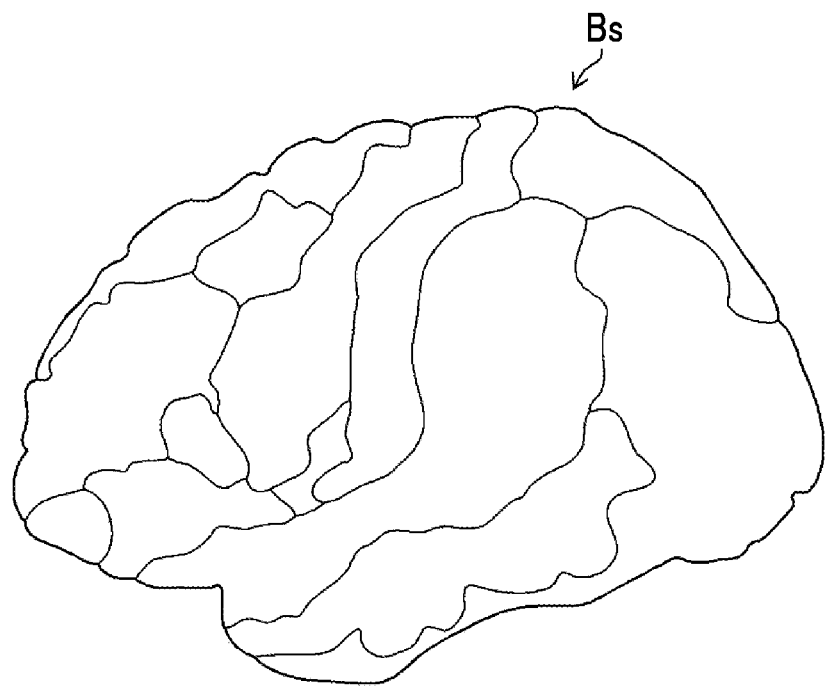
FIG. 3 is a diagram showing a standard brain image including division information.

FIG. 3 is a diagram showing an example of the standard brain image Bs including division information, and the entire brain is divided into a plurality of brain areas. In this example, the standard brain image Bs is divided into a plurality of brain areas. For example, the standard brain image Bs is divided into a plurality of brain areas according to the Broadmann's brain map. In the brain area, a ventricle and a cavity other than the ventricle (a cavity filled with cerebrospinal fluid) may be the brain area.

The image acquisition unit 12A can acquire the standard brain image Bs from the storage 16 or the PACS 2. In addition, the image acquisition unit 12A can acquire a first brain image B1 (FIG. 4) and a second brain image B2 (not shown) of the same subject having different imaging dates and times from the PACS 2 or the electronic medical record 3. In this example, the first brain image B1 has an imaging date and time earlier than that of the second brain image B2, for example, an image six months or one year ago.

The data acquisition unit 12B acquires a table T3 shown in FIG. 6, diagnostic information (in this example, diagnostic data indicating a test result in ADAS) D1 shown in FIG.

9, and the like. The table T3 and the diagnostic data D1 are used for display control of medical images and medical information in a case where the medical information display apparatus 1 functions as a viewer.

In the table T3 shown in FIG. 6, numbers indicating brain areas (Broadmann field: 1 to 52) and descriptions of name and function of each brain area are stored so as to be associated with each other. Known data can be used as the data of the table T3. The table T3 can be stored in the storage 16 in advance, and can be read and used appropriately.

Figure 7:
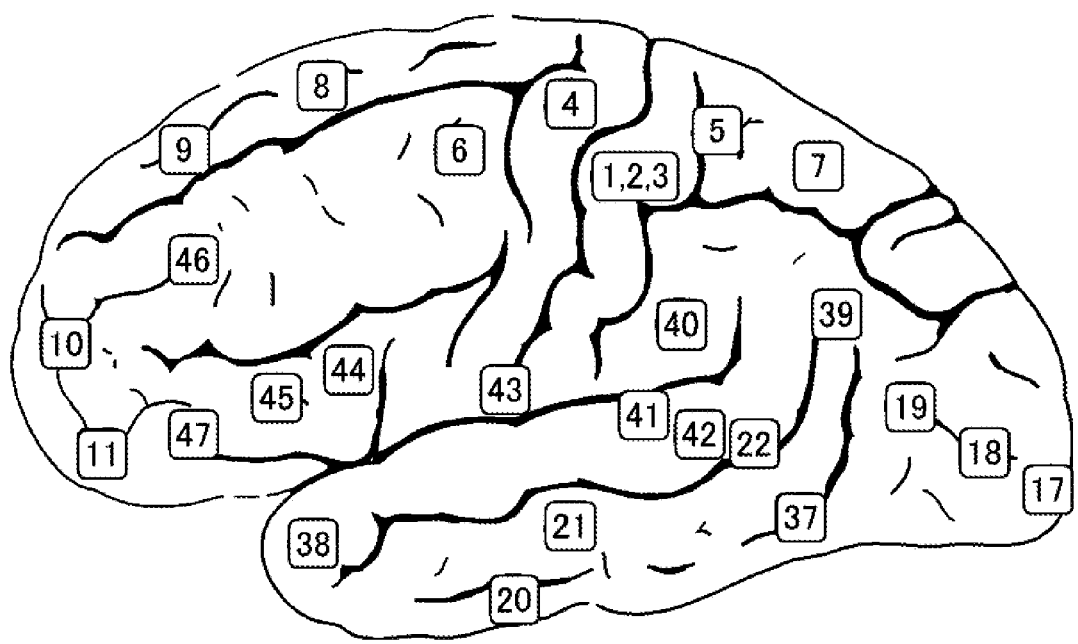
FIG. 7 is a diagram in which a brain image on the outer surface is numbered to indicate brain areas.
Figure 8:
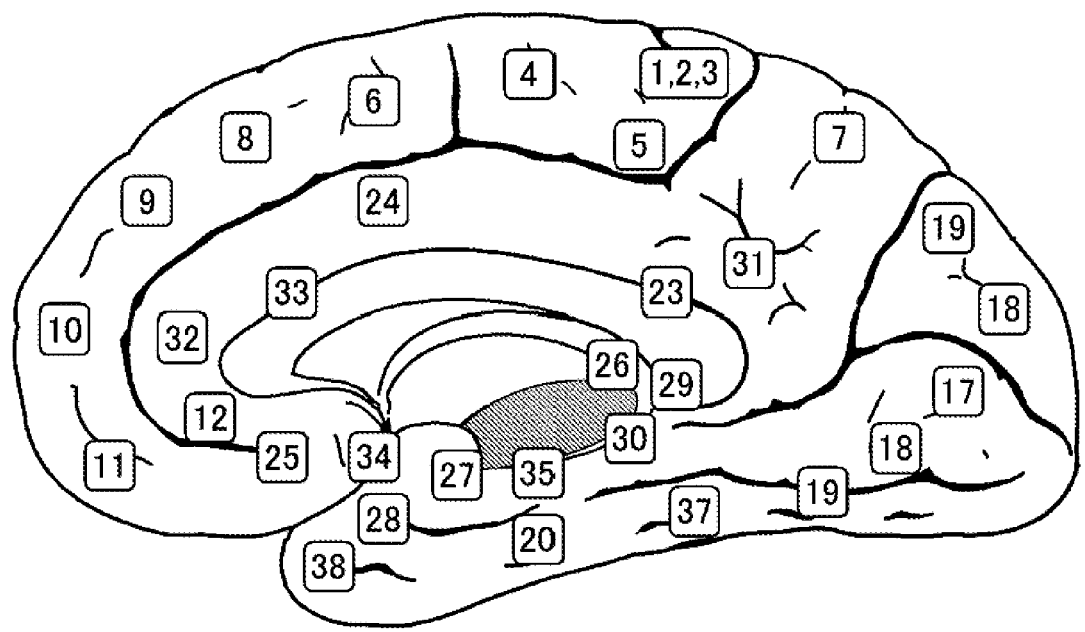
FIG. 8 is a diagram in which a brain image on the inner surface is numbered to indicate brain areas.

FIG. 7 is a diagram in which a brain image on the outer surface is numbered to indicate brain areas, and FIG. 8 is a diagram in which a brain image on the inner surface is numbered to indicate brain areas.

The ADAS is one of various cognitive function evaluations. The ADAS is for evaluating the cognitive function centered on memory in order to test dementia. As shown in FIG. 9, evaluation is performed based on eleven test items of word reproducibility, spoken language ability, auditory comprehension of language, difficulty in speaking in spontaneous speech, according to verbal command, finger and article designation, constructive action, idea movement, orientation, word recognition, and test teaching reproducibility and the ADAS score of 0 to 70 points. The score is obtained by subtracting the number of correct answers from the full score of each test item. In a case where all questions are correct, the score is 0. In the example shown in FIG. 9, there are errors in 35 questions. For example, the test item 4 "difficulty in speaking in spontaneous speech" is wrong in 4 of 5 questions.

The data acquisition unit 12B can acquire diagnostic data D1 (FIG. 9) indicating the ADAS test result from, for example, the electronic medical record 3 or the header portion of the image file complying with the DICOM standard. The cognitive function evaluation is not limited to ADAS and ADAS-Jcog, and mini mental state examination (MMSE), Wechsler adult intelligence scale-III (WAIS-III), revised Hasegawa type simple intelligence evaluation scale, and the like can be used.

Returning to FIG. 2, the brain area division unit 12C is a unit that divides each of the three-dimensional first brain image B1 and the three-dimensional second brain image B2 into a plurality of brain areas.

Figure 4:
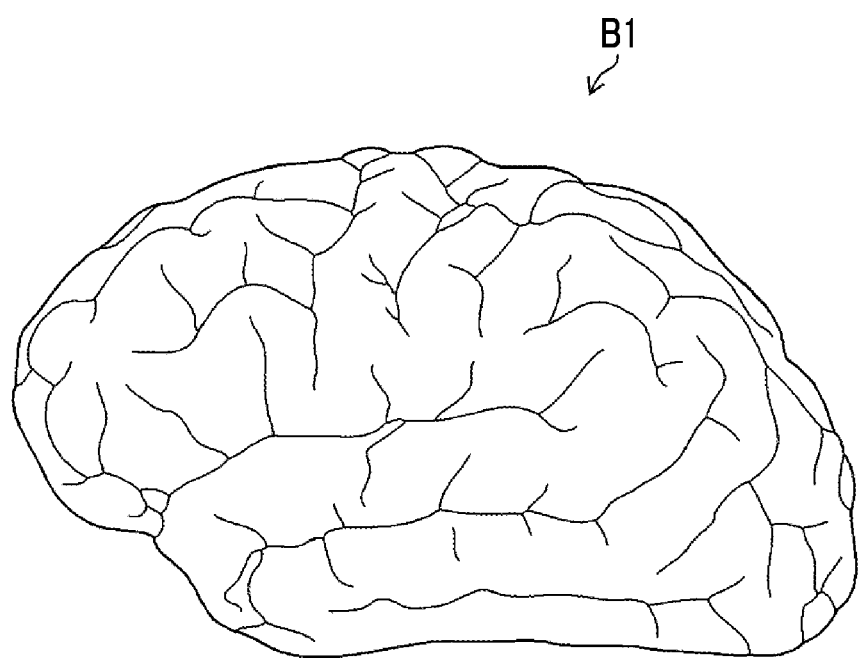
FIG. 4 is a diagram showing a first brain image.

First, the brain area division unit 12C performs registration between the standard brain image Bs shown in FIG. 3 and the first brain image B1 shown in FIG. 4. The size and shape of the brain vary from person to person. For example, in a case where the brain is compared with the standard brain, the size and shape of the brain are different by about +15% at the maximum.

The standard brain image Bs and the first brain image B1 have different sizes and shapes. Therefore, in order to divide the first brain image B1 into a plurality of brain areas, the brain area division unit 12C performs first registration using landmarks common to the standard brain image Bs and the first brain image B1.

As landmarks, specifically, feature points of characteristic regions, such as a number of cerebral sulci (upper frontal sulcus, inferior frontal sulcus, lateral sulcus, longitudinal cerebral fissure, and the like) and ventricles (left and right lateral ventricles of the cerebral hemisphere, third ventricle, and fourth ventricle) included in the brain, can be used. In this example, it is assumed that the standard brain image Bs is registrated with the first brain image B1. This is because causing no deformation of the first brain image B1 can improve the calculation accuracy of the analysis value (such as the atrophy rate of the brain area) by the image analysis unit 12D to be described later.

The brain area division unit 12C extracts landmarks from the standard brain image Bs and the first brain image B1 for registration. For example, landmarks may be extracted by template matching using a template indicating a landmark, or may be extracted using a discriminator that has been learned to discriminate landmarks included in an image.

The brain area division unit 12C performs first registration so that corresponding landmarks (feature points) match each other between the standard brain image Bs and the first brain image B1. In the present embodiment, the first registration is registration by similarity transformation. Specifically, the first registration is registration by parallel movement, rotation, and similar enlargement and reduction of the standard brain image Bs. The brain area division unit 12C performs the first registration by performing similarity transformation of the standard brain image Bs so that the correlation between the landmark included in the standard brain image Bs and the corresponding landmark included in the first brain image B1 is maximized.

After performing the first registration, the brain area division unit 12C performs second registration for matching the standard brain image Bs with the first brain image B1 using the corresponding landmarks. The second registration is registration by nonlinear transformation. As the registration by nonlinear transformation, for example, there is registration performed by nonlinearly transforming pixel positions using functions, such as B spline and thin plate spline.

The brain area division unit 12C performs the second registration by nonlinearly transforming each pixel position of the standard brain image Bs after the first registration into a corresponding pixel position included in the first brain image B1.

Figure 5:
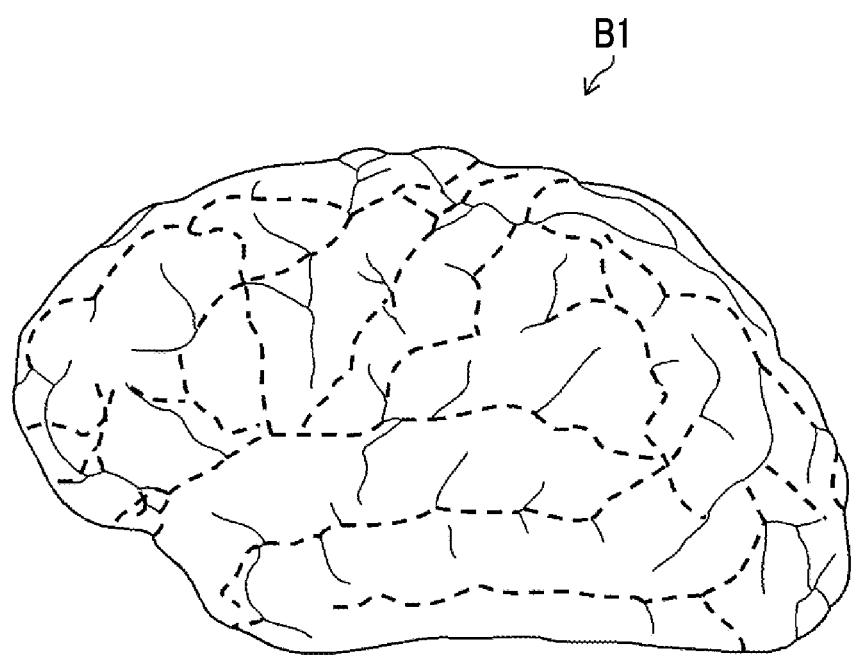
FIG. 5 is a diagram showing a first brain image divided into a plurality of brain areas.

By applying three-dimensional information (division information after registration) of the boundary between brain areas divided in the standard brain image Bs to the first brain image B1 after registrating the standard brain image Bs with the first brain image B1 as described above, the brain area division unit 12C can divide the first brain image B1 into a plurality of brain areas as shown by the broken lines in FIG. 5.

The brain area division unit 12C divides the second brain image B2 into brain areas. Specifically, third registration is performed using landmarks between the first brain image B1 and the second brain image B2. In the third registration, image enlargement and reduction are not performed, and parallel movement and rotation of the first brain image B1 are performed to registrate the first brain image B1 with the second brain image B2. Alternatively, the second brain image B2 may be registrated with the first brain image B1.

Since the first brain image B1 and the second brain image B2 are brain images of the same subject having different imaging dates and times, both the brain images after the third registration have a very high degree of matching. That is, the three-dimensional position of a certain pixel (voxel) in the three-dimensional first brain image B1 and a voxel of the second brain image B2 corresponding to the voxel are present at the same three-dimensional position or the vicinity thereof.

Therefore, the brain area division unit 12C can match each voxel of the first brain image B1 and each voxel of the second brain image B2 with each other by corresponding point matching based on local image features centered on the corresponding voxels, for example.

The brain area division unit 12C can divide the second brain image B2 into a plurality of brain areas by performing matching between all voxels of each voxel of the first brain image B1 and each voxel of the second brain image B2. That is, three-dimensional information of each voxel of the second brain image B2 acquired by acquiring three-dimensional information of each voxel of the second brain image B2 corresponding to each voxel (that is, a voxel based on the division information) of the boundary of the plurality of brain areas of the first brain image B1 is division information for dividing the second brain image B2 into a plurality of brain areas.

The method of dividing the first brain image B1 and the second brain image B2 into a plurality of brain areas by the brain area division unit 12C is not limited to the embodiment described above, and various known methods can be applied. For example, a method described in JP2011-010828A can be applied.

The brain area division unit 12C divides the first brain image B1 into a plurality of brain areas so that three-dimensional information (coordinates x, y, z) and brain area labels (numbers indicating brain areas) and/or names are associated with each other for all voxels forming the three-dimensional first brain image B1 as shown in FIG. 10, and temporarily stores the results in the main memory 14 or stores the results in the storage 16. Similarly, also for the second brain image B2, three-dimensional information and brain area labels and the like are associated with each other for all voxels, and the results are stored in the main memory 14 or the storage 16. In addition, it is preferable to store the correspondence between each voxel of the first brain image B1 and each voxel of the second brain image B2. This is because a voxel movement vector can be calculated based on the three-dimensional information between corresponding voxels.

Each coordinate axis of the three-dimensional information (coordinates x, y, z) of the brain image corresponds to each body axis (X axis: left-right, Y axis: back-abdomen, Z axis: head-tail). The origin (0, 0, 0) can be set at a specific position outside or inside the brain, for example.

The image analysis unit 12D is a unit that analyzes the first brain image B1 and the second brain image B2 for each divided brain area and outputs an analysis result (analysis value). For example, analysis results, such as an atrophy rate, a volume change amount, a shape change amount, a Z score, and a blood flow volume for each brain area, are output.

Figure 11:
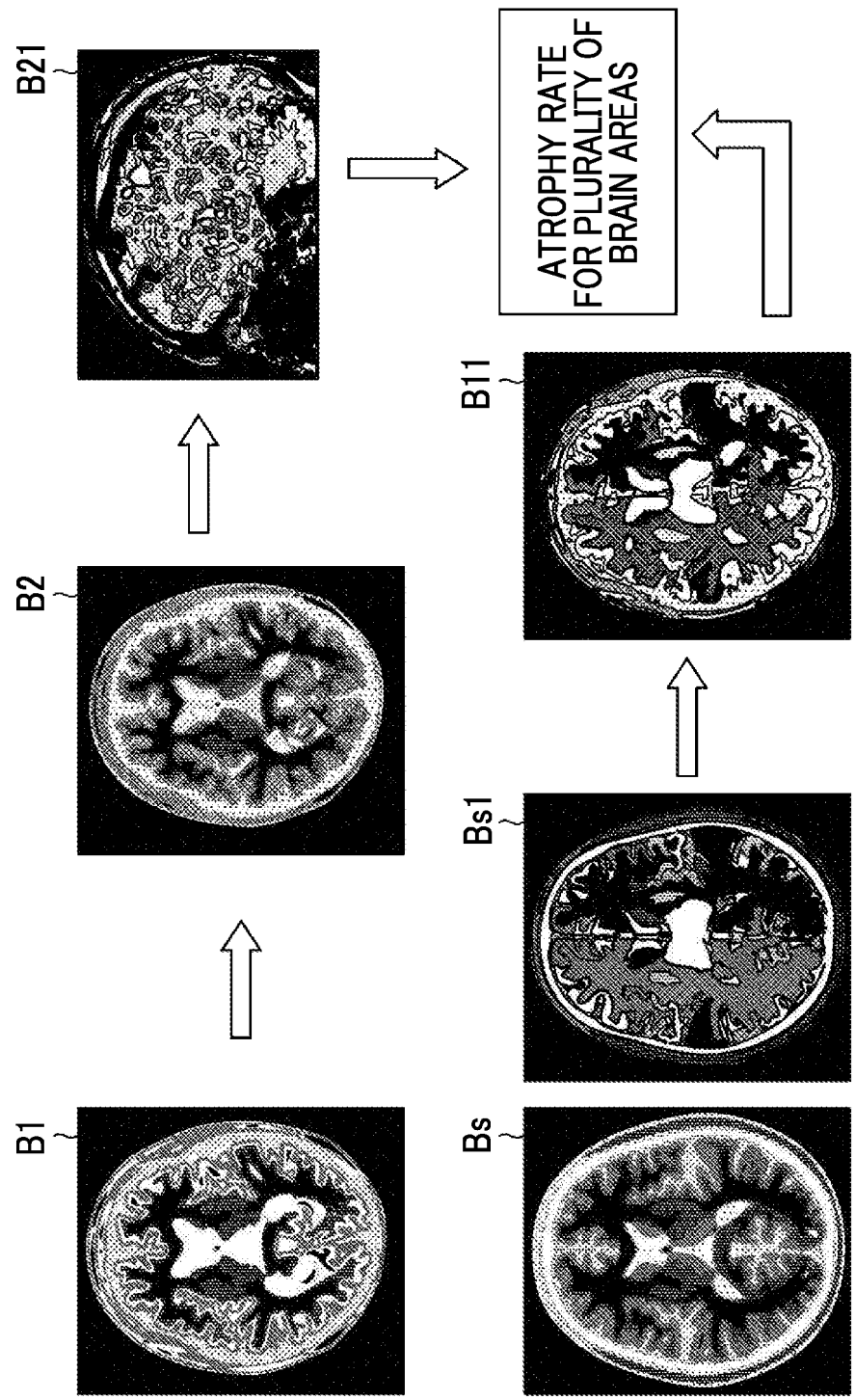
FIG. 11 is a diagram showing the flow of a process of a brain area division unit and a process of an image analysis unit.

FIG. 11 is a diagram showing the flow of processing of the brain area division unit 12C and processing of the image analysis unit 12D.

In FIG. 11, the standard brain image Bs includes division information for dividing the entire brain into a plurality of brain areas. Bsl indicates a plurality of brain areas (division information) of the standard brain image Bs. By registering the standard brain image Bs with the first brain image B1, division information indicating the plurality of brain areas of the standard brain image Bs after the registration can be used as division information (B11) indicating the plurality of brain areas of the first brain image B1.

By applying the first brain image B1 having the division information of the plurality of brain areas to the second brain image B2 and performing association between the voxels, the second brain image B2 can be substantially divided into the plurality of brain areas. B21 is a diagram showing a plurality of brain areas of the second brain image B2. B11 indicates a plurality of brain areas of the first brain image B1 in the axial section, and B21 indicates a plurality of brain areas of the second brain image B2 in the sagittal section.

The image analysis unit 12D calculates the volumes of the plurality of brain areas of the first brain image B1 and the plurality of brain areas of the second brain image B2 for each same brain area. After calculating the volume, the atrophy rate of the brain is calculated as an analysis value for each brain area by subtracting the volume of the corresponding brain area of the second brain image B2 from the volume of the brain area of the first brain image B1 and dividing a value obtained as a result of the subtraction by the volume of the corresponding brain area of the first brain image B1.

The brain area atrophies in a case where the atrophy rate is a positive value, and expands in a case where the atrophy rate is a negative value. The volume of the brain area can be calculated by counting the number of voxels in the brain area (the volume per voxel is known).

In this example, the image analysis unit 12D calculates the atrophy rate as an analysis value for each of the plurality of brain areas. However, the volume change amount, the shape change amount, the Z score, and the blood flow volume for each brain area may be calculated as analysis values.

The volume change amount for each brain area can be calculated by subtracting the volume of the corresponding brain area of the first brain image B1 from the volume of the brain area of the second brain image B2.

The shape change amount can be calculated from the change amount of the sphericity of the corresponding brain areas of the first brain image B1 and the second brain image B2, for example. The sphericity can be determined by the ratio of the surface area of a sphere having the same volume as the brain area to the surface area of the brain area. In addition, the sphericity can be determined by calculating the absolute value of a change region between the brain area of the first brain image B1 and the corresponding brain area of the second brain image B2.

The Z score can be calculated for each brain area of the first brain image B1 and the second brain image B2 based on the following equation.

$$Z = (x_{ave} - x)/\sigma \quad \text{[Equation 1]}$$

Here, x: voxel value, $x_{ave}$: average value of voxel values of healthy persons, $\sigma$: standard deviation of voxel values of healthy persons.

The image analysis unit 12D can calculate the blood flow volume for the first brain image B1 and the second brain image B2 by an arterial spin labeling (ASL) brain perfusion examination for evaluating the blood flow dynamics of the brain without using a contrast medium.

Figure 12:
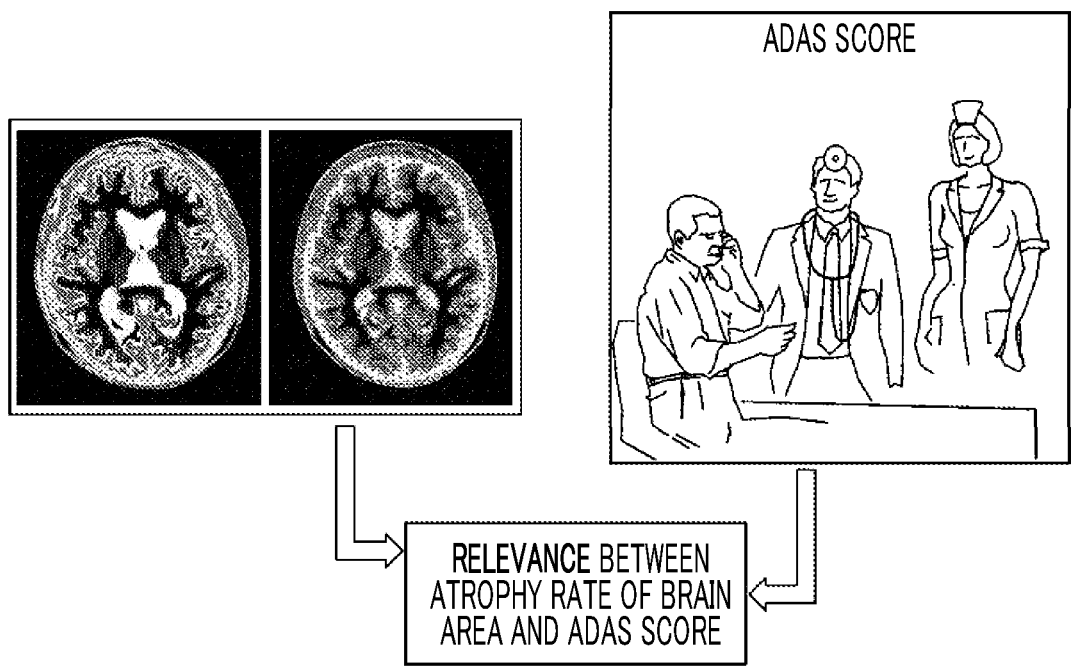
FIG. 12 is a diagram used to describe the creation of a first table.

The information processing unit 12E is a unit that calculates the relevance between a plurality of divided brain areas of the brain image and a plurality of test items of the diagnostic test for dementia and creates a table (first table T1 (FIG. 16)) that stores the relevance between a plurality of brain areas (in this example, brain areas of 1 to 52) and a plurality of test items (in this example, test items of 1 to 11). As shown in FIG. 12, an analysis value for each brain area of the brain image of the patient (in this example, an atrophy rate of each brain area) and the test result of the diagnostic test for dementia (in this example, the ADAS score) are collected, and the relevance between the atrophy rate and the test items is calculated.

Specifically, in creating the first table T1, the information processing unit 12E acquires the atrophy rate of each brain area of brain images of a number of patients and the score for each of the eleven test items of the ADAS from the image analysis unit 12D and the data acquisition unit 12B.

Figure 13:
FIG. 13 is a correlation diagram showing correlation between the score and the atrophy rate of a test item.
Figure 14:
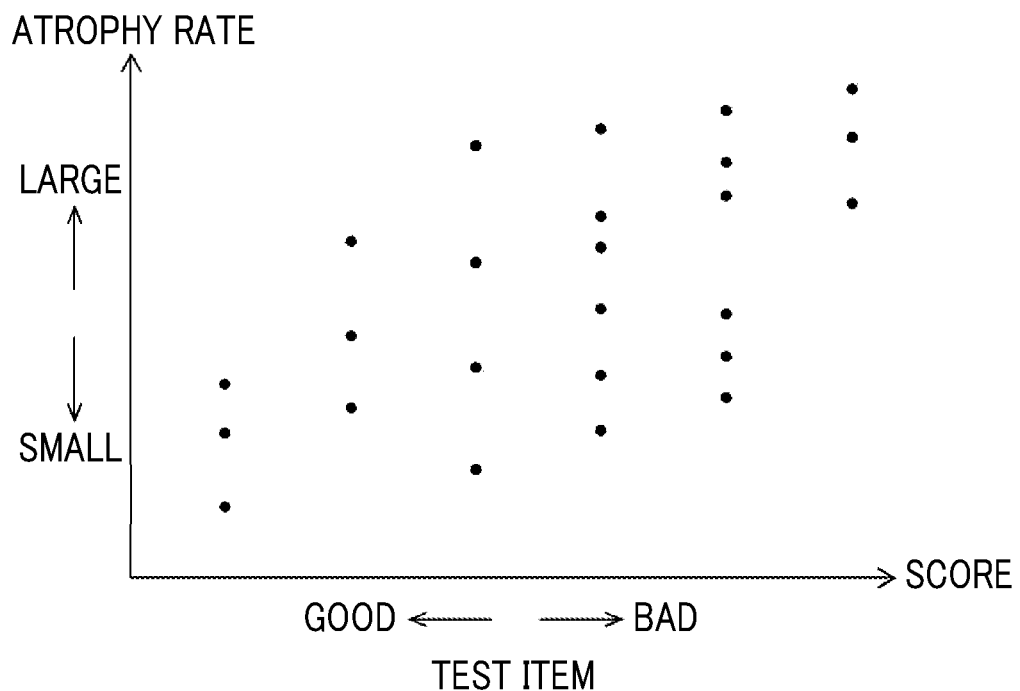
FIG. 14 is another correlation diagram showing correlation between the score and the atrophy rate of a test item.
Figure 15:
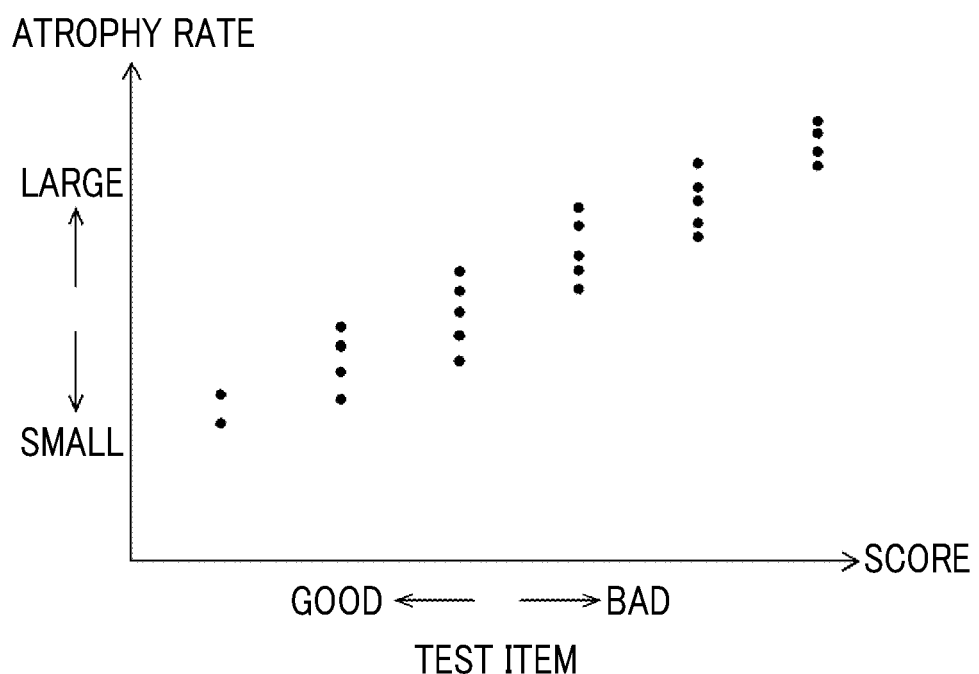
FIG. 15 is still another correlation diagram showing correlation between the score and the atrophy rate of a test item.

FIGS. 13 to 15 are correlation diagrams showing the correlation between the score of each test item and the atrophy rate.

The horizontal axis in the correlation diagrams shown in FIGS. 13 to 15 indicates one test item of the eleven test items of ADAS, and the vertical axis in the correlation diagrams indicates the atrophy rate of one brain area of a plurality of brain areas. In the ADAS, the number of correct answers is subtracted from the full score of the test item to obtain a score. Therefore, the higher the score, the more incorrect answers and the worse the evaluation of the cognitive function.

FIG. 13 shows a case where there is almost no correlation between the score of the test item and the atrophy rate, FIG. 14 shows a positive weak correlation, and FIG. 15 shows a positive strong correlation.

The information processing unit 12E calculates the relevance between the atrophy rate of each brain area of the brain image and the score for each test item, and creates the first table T1 indicating the relevance as shown in FIG. 16.

In FIG. 16, $A_{i,j}$ ($1 \leq i \leq 52$, $1 \leq j \leq 11$) indicates the relevance, and can be a correlation value of $-1 \leq A_{i,j} \leq 1$. In the brain area, atrophy progresses over time. However, for example, in a case where the ventricle and other cavities are divided as brain areas, the brain area expands. Therefore, in this case, a negative correlation value is obtained. In addition, FIG. 16 shows the relevance ($A_{20,1}$=0.45, $A_{22,1}$=0.30) between the test item (item 1) of ADAS and the brain areas (lower temporal gyms, upper temporal gyms) indicated by numbers 20 and 22. However, these relevance values are not actually calculated values.

The first table T1 created by the information processing unit 12E is stored in, for example, the storage 16, and is appropriately used as necessary by the display controller 12F or the like. In addition, it is preferable that the first table T1 is periodically updated by the information processing unit 12E. This is because a more reliable table can be obtained by creating the first table T1 using the analysis values and the diagnostic tests for each brain area of a larger number of patients. The first table T1 created by an apparatus or a system outside the medical information display apparatus 1 may be used. In this case, the information processing unit 12E is not necessary.

The display controller 12F generates a display image for displaying, for example, a medical image (at least one brain image of the first brain image B1 or the second brain image B2) or medical information (analysis value obtained by performing analysis for each brain area of the first brain image B1 and second brain image B2, the table T3, and the diagnostic data D1) on the monitor 24 and outputs the generated display image to the monitor 24, and has a function as an output unit.

Figure 17:
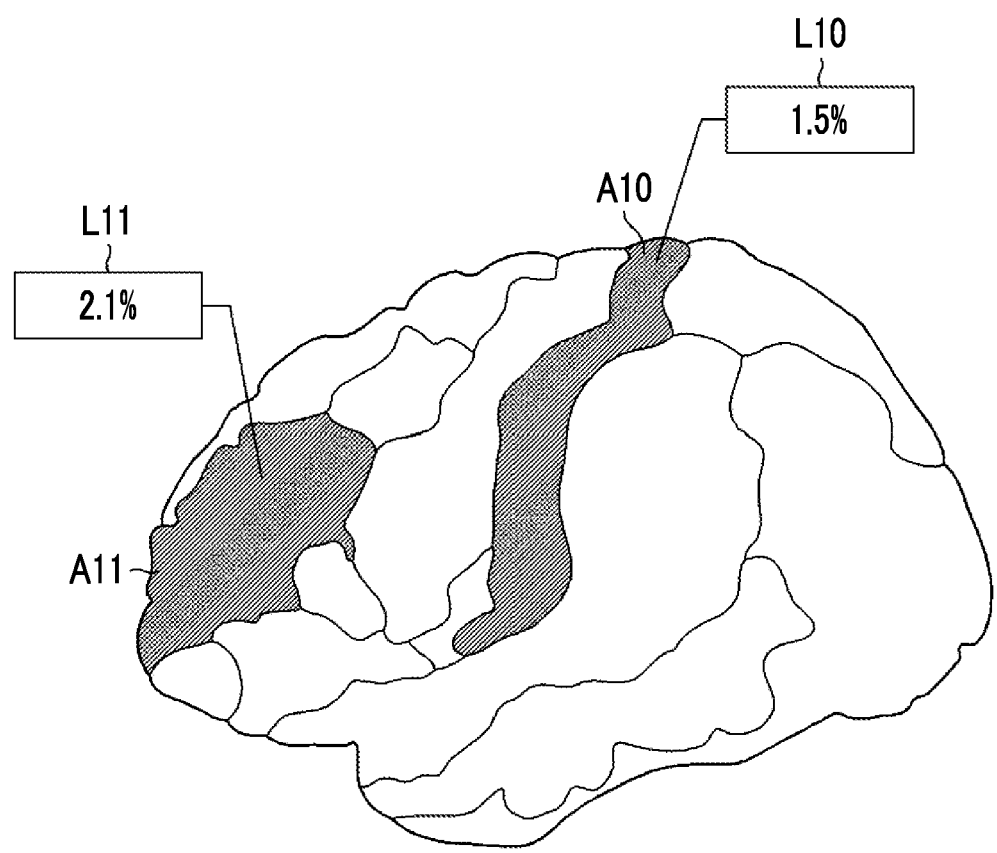
FIG. 17 is a diagram showing an example of a medical image and medical information displayed on a monitor.

FIG. 17 is a diagram showing an example of a medical image and medical information displayed on the monitor 24.

In the example shown in FIG. 17, brain areas A10 and A11 having large atrophy rates (brain areas where the atrophy rate exceeds a threshold value) are displayed so as to be distinguishable from other brain areas as indicated by hatching. For example, by giving a red color to the brain areas A10 and A11, the brain areas A10 and A11 can be displayed so as to be distinguishable from other brain areas by different colors. In addition, labels L10 and L11 can be given to the brain areas A10 and A11. As the labels L10 and L11, analysis values (in the example shown in FIG. 17, an atrophy rate expressed as a percentage) are given. In addition, numbers (Broadmann field: 1 to 52) indicating the brain areas A10 and A11, the name of the brain area, or the like may be displayed.

The display controller 12F can display necessary medical images and medical information on the monitor 24 according to the operation of the operation unit 22 by the doctor.

<Display Control of Brain Image>

Hereinafter, display control of the brain image in the medical information display apparatus 1 will be described. In the present embodiment, a doctor's diagnosis of dementia is supported by extracting and displaying a cavity region of the brain including the ventricle from the brain images of the patient at two time points.

Figure 18:
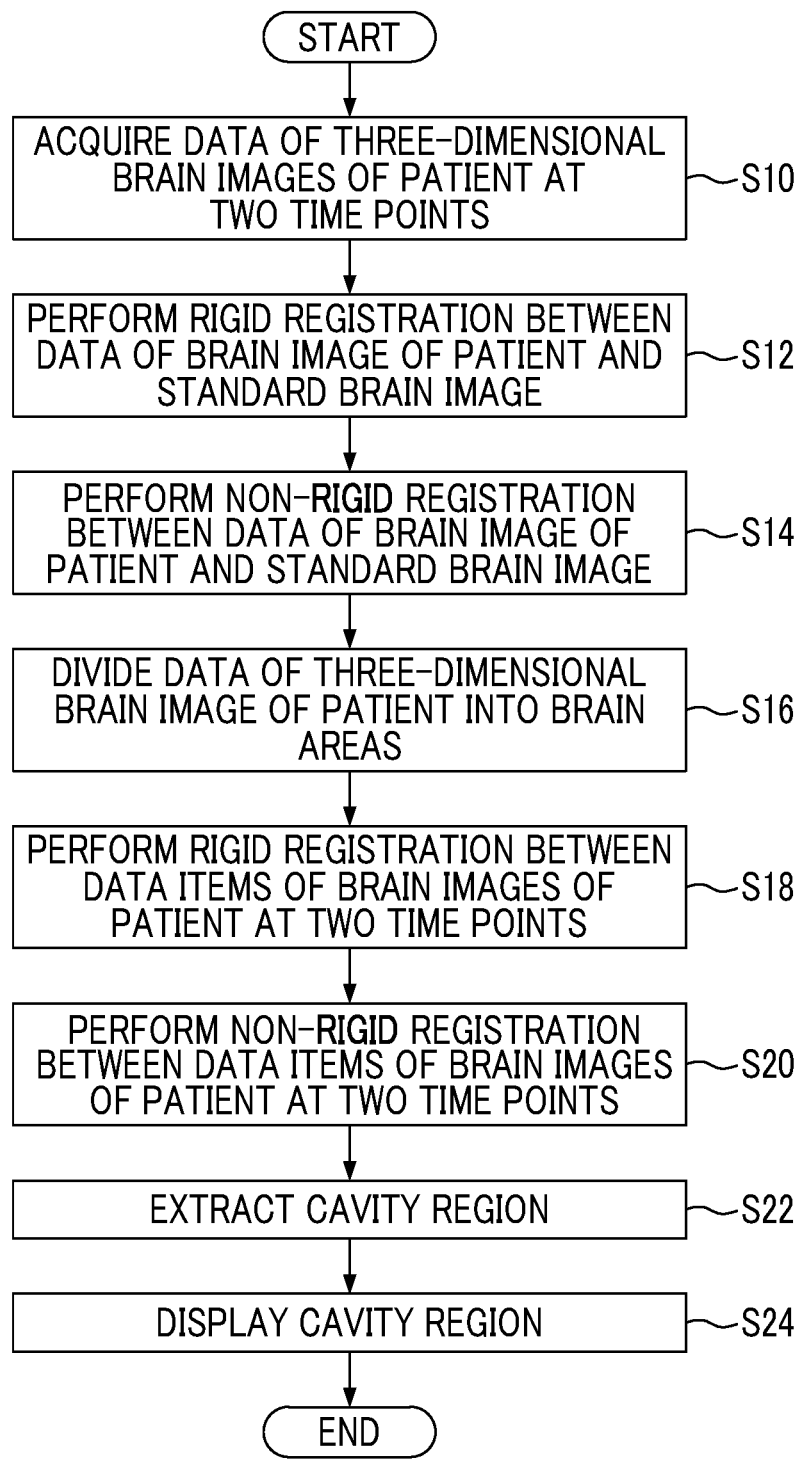
FIG. 18 is a flowchart relating to display control of the medical information in the medical information display apparatus.

FIG. 18 is a flowchart relating to display control of the medical information in the medical information display apparatus 1.

As shown in FIG. 18, first, the data acquisition unit 12B receives and acquires an input of data of three-dimensional brain images of a patient at two time points (step S10). In the following description, in the data of the three-dimensional brain images of the patient at two time points, the brain images of a patient captured at a first time point and a second time point later in time than the first time point are referred to as a first brain image and a second brain image, respectively.

The data acquisition unit 12B can acquire an MRI image captured under various imaging conditions as a brain image. Types of the MRI image include, for example, a T1 weighted image (T1WI), a T2 weighted image (T2WI), a fluid attenuated inversion recovery (FLAIR) image, a T2*weighted image (T2*WI), a diffusion weighted image (DWI), or the like.

In the T1WI, a signal intensity of water is lower than that of the cerebral cortex, and the water is depicted in black. For this reason, in the T1WI, the ventricle (a space in the brain where a cerebrospinal fluid is produced) is black. The T1WI has a feature that an anatomical structure such as the cerebral cortex (gray matter) and the white matter is easily grasped.

In the T2WI, a signal intensity of water is higher than that of the cerebral cortex, and the water is depicted in white. For this reason, in the T2WI, the ventricle is white. The T2WI is useful for extracting lesions because many lesions are depicted with a high signal.

The FLAIR image is a T2 weighted image in which a signal of water is suppressed, and the ventricle is depicted in black, and the lesion adjacent to the ventricle is clearly depicted.

The T2*WI is an image in which a hemorrhagic lesion is depicted in black, and is an image suitable for detecting a minute hemorrhagic lesion.

The DWI is an image obtained by imaging a diffusion motion (free mobility) of water molecules, and a signal intensity in a region where the diffusion of water molecules is decreased is relatively high and the region is depicted in white. In acute cerebral infarction, the diffusion of water molecules decreases, which is useful for determining the region of hyperacute cerebral infarction.

The medical information display apparatus 1 according to the present embodiment receives a designated input for a diagnosis purpose from an operator (a doctor or the like) by the operation unit 22. The information processing unit 12E can specify the type of an MRI image necessary for the diagnosis according to the diagnosis purpose designated by the operation unit 22, and acquire the specified type of image from the MRI apparatus 4. In the present embodiment, for example, the T1WI or T2WI image can be used to detect a change of the ventricle which is a cavity in the brain. In the following description, an example using the T1WI in which the ventricle is depicted in black will be described.

In the present embodiment, the type of image to be acquired by the data acquisition unit 12B may be directly designated by the operation unit 22 instead of the diagnosis purpose. In addition, in a case where the diagnosis purpose is designated, the types of images suitable for the diagnosis purpose are listed so that the data acquisition unit 12B can select an image to be acquired from the list of the types of images. The diagnosis purpose is designated before the image of the patient is captured, and it may be possible to provide an instruction of the kind of image to be captured to an operator (medical radiology technician or the like) of the MRI apparatus 4 in accordance with designation of the diagnosis purpose.

Next, the image analysis unit 12D performs rigid registration between one of the first brain image and the second brain image and a standard brain image showing a standard brain model based on a Broadmann's brain map (step S12), and performs non-rigid registration therebetween (step S14). In the following description, description will be made assuming that the registration between the first brain image and the standard brain image, but the registration between the second brain image and the standard brain image may be performed. Here, the rigid registration includes, for example, a process of aligning respective centroid positions and orientations without deforming an image to be registrated. The non-rigid registration includes a process of projecting a brain area included in the standard brain image onto the brain image of the patient by deforming the standard brain image and aligning it with the first brain image.

Next, the brain area division unit 12C divides the three-dimensional brain image of the patient into a plurality of brain areas by using results of the registration in steps S12 and S14 (step S16). The brain area division is performed based on results of a brain activation test, for example, statistical data showing a relationship between a function of the brain and a blood flow volume obtained by measuring the blood flow volume with a positron emission tomography (PET) scanner during the activity of the brain.

Next, rigid registration (step S18) and non-rigid registration (step S20) are performed between the first brain image and the second brain image. Therefore, results of the brain area division of the first brain image in step S16 can be reflected in the second brain image.

Next, the image analysis unit 12D performs image analysis and extracts a cavity region from the first brain image and the second brain image (step S22), and the display controller 12F displays a brain image including the cavity region on the monitor 24 (step S24).

In the T1WI, the cavity region is a region having a relatively low signal value, and is depicted in black, so that a region having a brightness equal to or lower than a predetermined threshold value can be extracted as the cavity region. On the other hand, in the T2WI, the cavity region is a region having a relatively high signal value, and is depicted in white, so that a region having a brightness equal to or higher than a predetermined threshold value can be extracted as the cavity region.

A method of extracting the cavity region is not limited to the above method. For example, a non-cavity region of the brain may be extracted by a known technique, and a portion that has not been extracted may be set as a cavity region. Alternatively, a cavity region may be set in division information of a standard brain Bs, the cavity region may be projected in registration with the standard brain Bs, and the cavity region may be obtained from the first and second brain images.

Then, a change of the cavity region in the first and second brain images, that is, the cavity expansion and contraction can be determined based on check whether voxels detected from the first and second brain images after registration are cavitied or non-cavitied, or registration results or contour changes.

In display of the brain image in the present embodiment, changes in size and shape of the cavity region can be easily visualized. In addition, based on the results of registration in steps S18 and S20, the image analysis unit 12D calculates the changes in size and shape for each brain area around the ventricle, so that the atrophy rate or expansion rate for each brain area is easily visualized.

In the present embodiment, the image analysis unit 12D may acquire an analysis value for each brain area by image analysis of the brain area. As an analysis value, for example, a volume change amount, a shape change amount, a Z score, a blood flow volume, and an evaluation value of infarction or bleeding obtained by comparing at least one of a past three-dimensional brain image of the same patient or a three-dimensional brain image model of a healthy person with the three-dimensional brain image of the patient, can be obtained. Among these, the evaluation value of the infarction can be obtained, for example, as the amount of change in the size and shape of an infarct occurrence area detected as a white area in the DWI. In addition, the evaluation value of the bleeding can be obtained, for example, as the amount of change in the size and shape of a hemorrhagic lesion area detected as a black area in the T2*WI. The types of analysis values in the present embodiment are not limited to those listed above.

Brain area specifying information for specifying each brain area, function and position information, and an analysis value obtained by image analysis of the image analysis unit 12D may be associated with each other and stored in the main memory 14 as an analysis result table (analysis result table T10 of FIG. 25).

Figure 19:
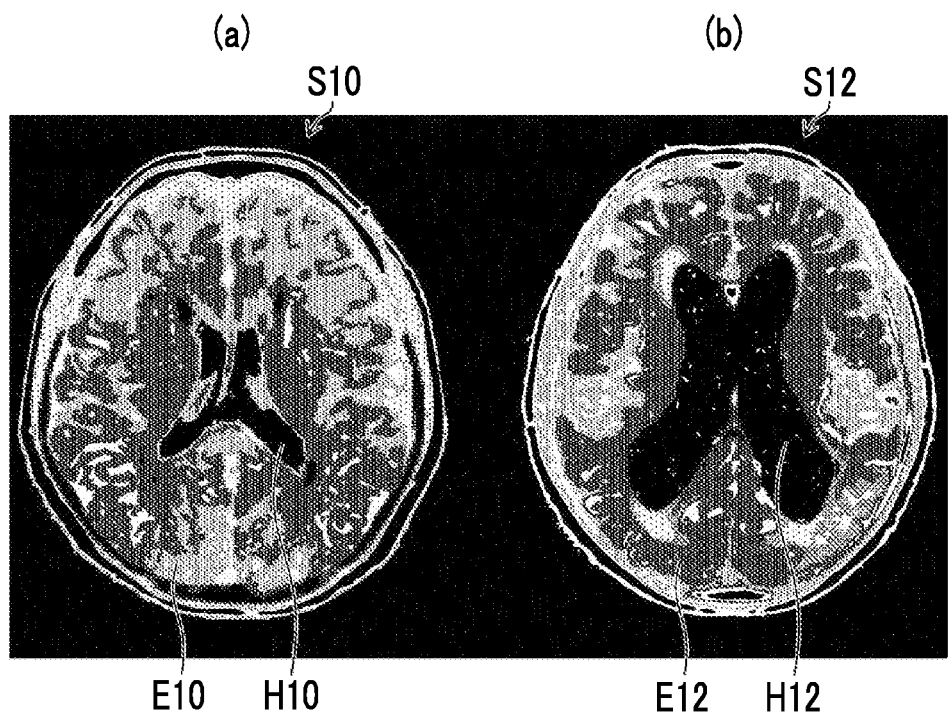
FIG. 19 is a diagram showing examples of brain images at two time points.

FIG. 19 is a diagram showing examples of brain images at two time points. (a) of FIG. 19 shows a brain image S10 at a first time point in the past, and (b) of FIG. 19 shows a brain image S12 at a second time point later than the first time point, for example, the current or latest time point.

In the example shown in FIG. 19, a ventricle H12 which is a cavity region in the brain image S12 at the second time point is larger than a ventricle H10 which is a cavity region in the brain image S10 at the first time point. That is, for a non-cavity region (for example, brain parenchyma) which is a part other than the cavity region, a second non-cavity region E12 at the second time point atrophies more than a first non-cavity region E10 at the first time point.

Figure 20:
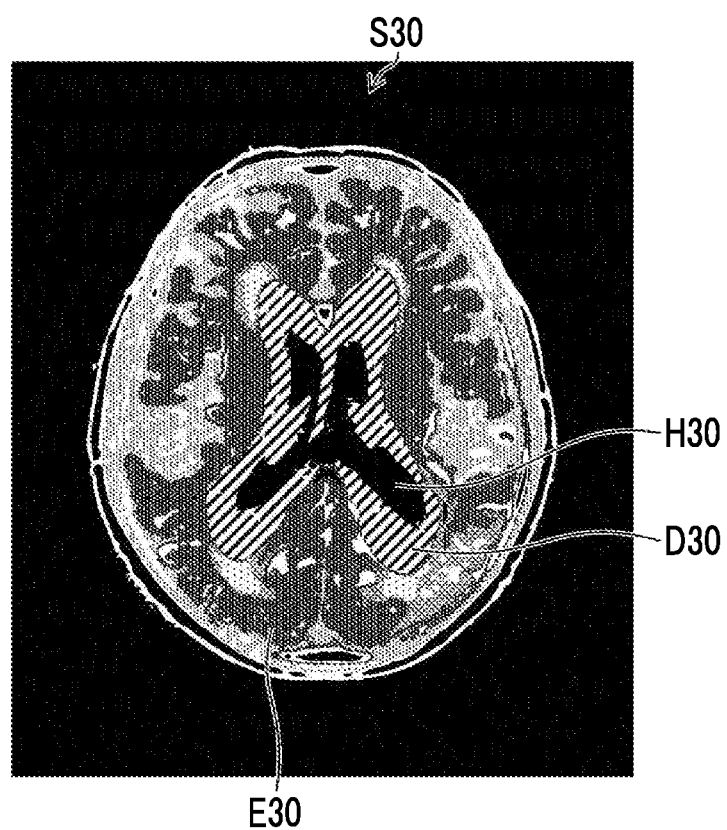
FIG. 20 is a diagram showing a display example of a cavity region corresponding to the example of FIG. 19.

FIG. 20 is a diagram showing a display example of a cavity region corresponding to the example of FIG. 19.

A brain image S30 shown in FIG. 20 is an image showing a difference between the brain image S12 at the second time point and the brain image S10 at the first time point. In the brain image S30, an increase amount of the ventricle that is the cavity region is shown as a cavity expansion part D30. A reference numeral E30 in the figure indicates a non-cavity part that is not the cavity region in both the first brain image S10 and the second brain image S12, and a reference numeral H30 indicates a cavity part that is the cavity region in both the first brain image S10 and the second brain image S12.

Figure 21:
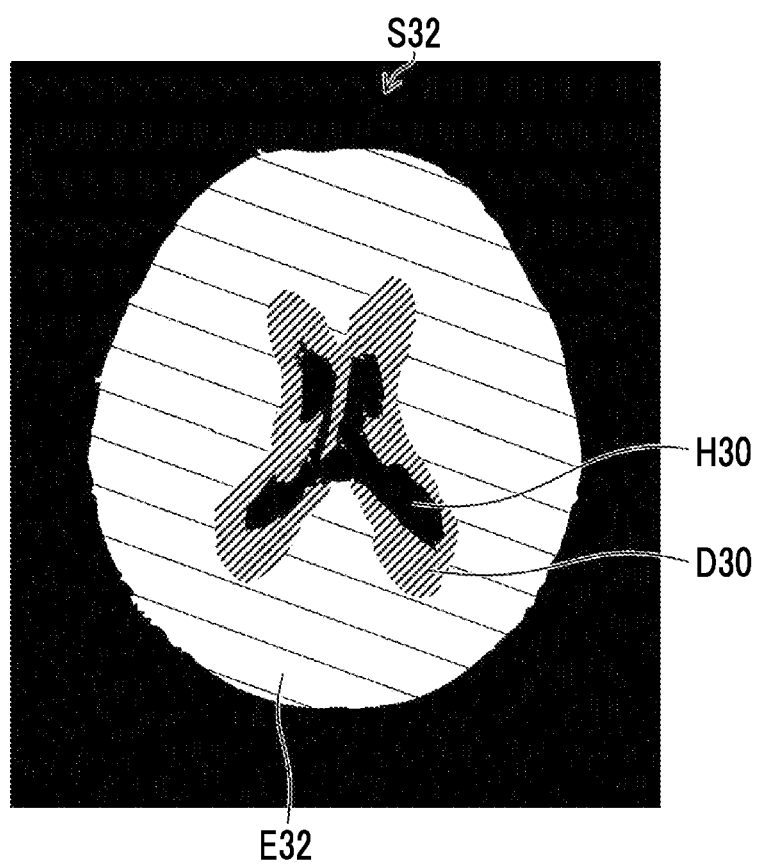
FIG. 21 is a diagram showing another display example of the cavity region.

As indicated by a reference numeral E32 in FIG. 21, a color, a brightness, or a transparency of the non-cavity part may be changed and displayed in a distinguishable manner from other regions.

Figure 22:
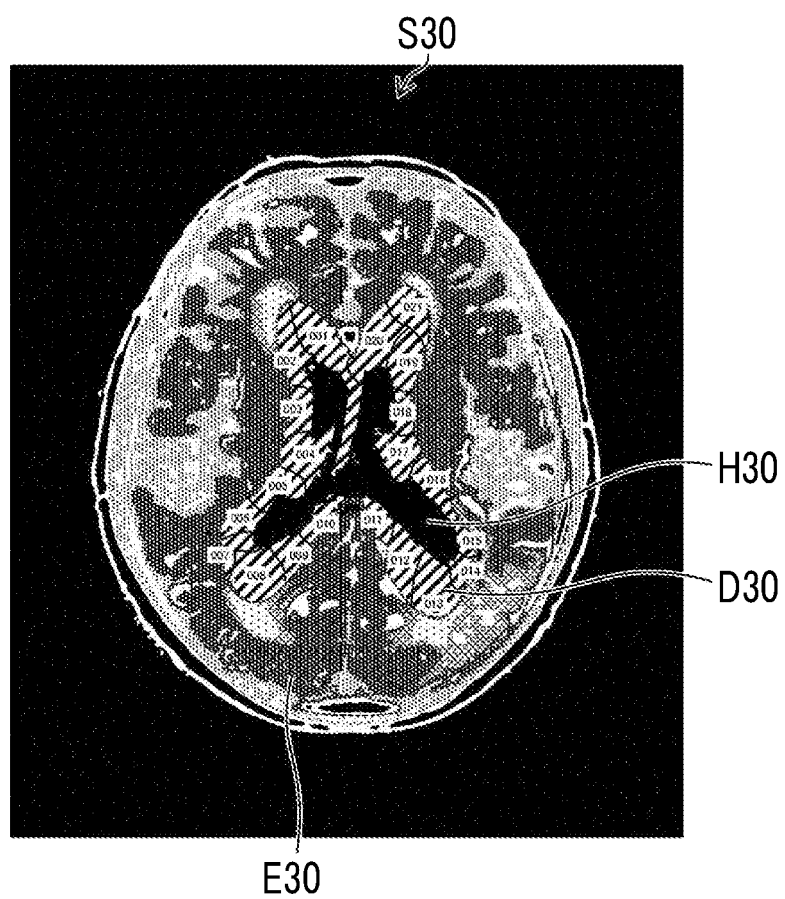
FIG. 22 is a diagram showing still another display example of the cavity region.

Further, as shown in FIG. 22, the atrophy rate for each brain area may be displayed. In the example shown in FIG. 22, for the brain areas included in a cavity expansion part D30, brain area specifying information including numbers and names indicating the brain areas, and functions and atrophy rates controlled by the brain areas are displayed. In the example shown in FIG. 22, the brain areas may be displayed in descending order of atrophy rate, for example. In addition, only the brain area whose the atrophy rate is larger than a threshold value may be displayed, or the brain area whose atrophy rate is up to the n-th order from the highest priority may be displayed.

Figure 23:
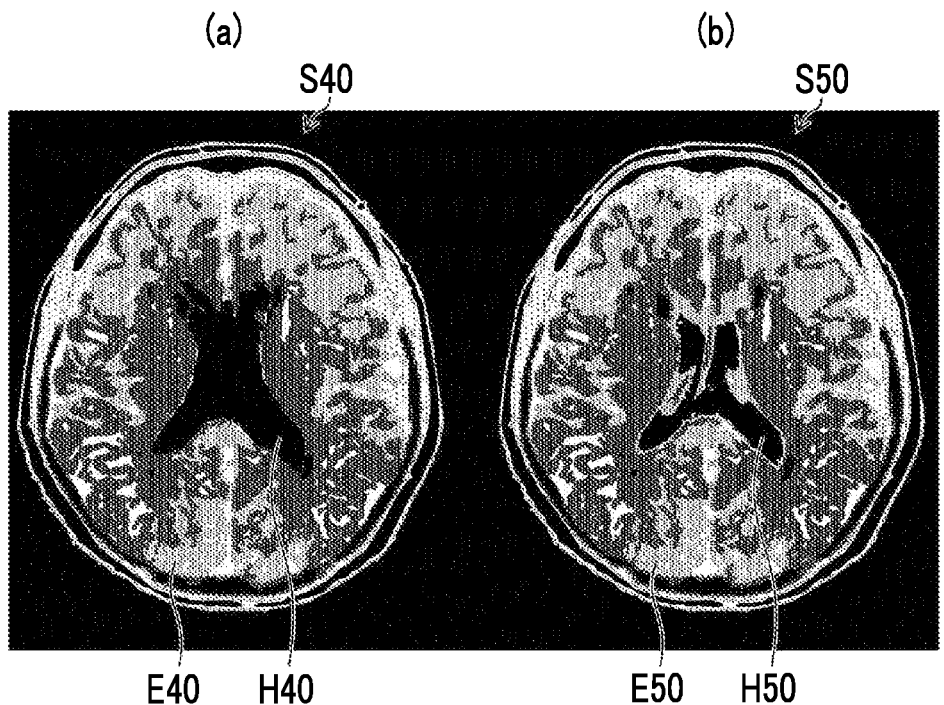
FIG. 23 is a diagram showing another example of brain images at two time points.

FIG. 23 is a diagram showing still another display example of the cavity region. (a) of FIG. 23 shows a brain image S40 at a first time point in the past, and (b) of FIG. 23 shows a brain image S50 at a second time point later than the first time point.

In the example shown in FIG. 23, a ventricle H50 which is a cavity region in the brain image S50 at the second time point is smaller than a ventricle H40 which is a cavity region in the brain image S40 at the first time point. That is, for a non-cavity region (for example, brain parenchyma) which is a part other than the cavity region, a second non-cavity region E50 at the second time point expands more than a first non-cavity region E40 at the first time point.

Figure 24:
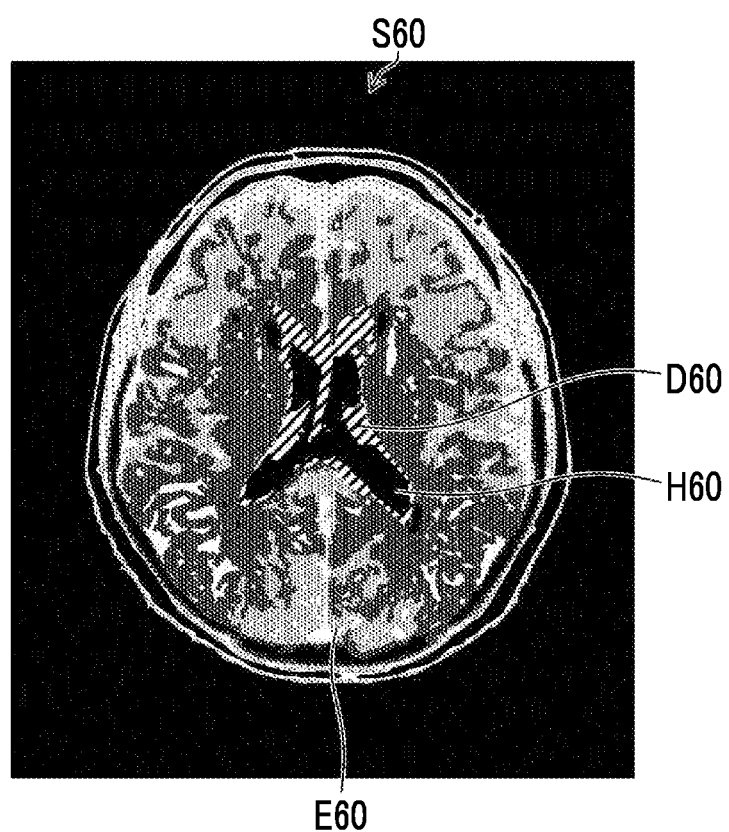
FIG. 24 is a diagram showing a display example of a cavity region corresponding to the example of FIG. 23.

FIG. 24 is a diagram showing a display example of a cavity region corresponding to the example of FIG. 23.

A brain image S60 shown in FIG. 24 is an image showing a difference between the brain image S50 at the second time point and the brain image S40 at the first time point. In the brain image S60, a decrease amount of the ventricle that is the cavity region is shown as a cavity contraction part D60. A reference numeral E60 in the figure indicates a non-cavity part that is not the cavity region in both the first brain image S40 and the second brain image S50, and a reference numeral H60 indicates a cavity part that is the cavity region in both the first brain image S40 and the second brain image S50.

Also in FIG. 24, as in the example shown in FIG. 22, it is possible to display the atrophy rate and expansion rate for each brain area.

According to the present embodiment, the atrophy state of the brain in the cavity region can be easily and appropriately displayed for the doctor by displaying a change of the cavity region of the brain. In this manner, it is possible to support a doctor's diagnosis of dementia.

In the present embodiment, the brain image showing a difference between the brain image at the second time point and the brain image at the first time point is displayed, but the present embodiment is not limited to this. For example, a three-dimensional image with transparent areas other than the cavity expansion part may be displayed.

The display controller 12F may display the test item corresponding to the brain area whose size or shape is changed in accordance with the change of the cavity region together with a table of FIG. 22 by using the first table T1 that stores the relevance between the plurality of brain areas and the plurality of test items shown in FIG. 16. Further, the display controller 12F may display analysis values other than the atrophy rate described below together with the table of FIG. 22.

In the present embodiment, it is also possible to display the analysis results of the brain area stored in the analysis result table. FIG. 25 is a diagram showing an example of an analysis result table.

In an analysis result table T10 shown in FIG. 25, numbers and names for designating brain areas are stored as brain area specifying information, and the brain area specifying information is stored in association with a function, a position, and an analysis value of each brain area.

Figure 26:
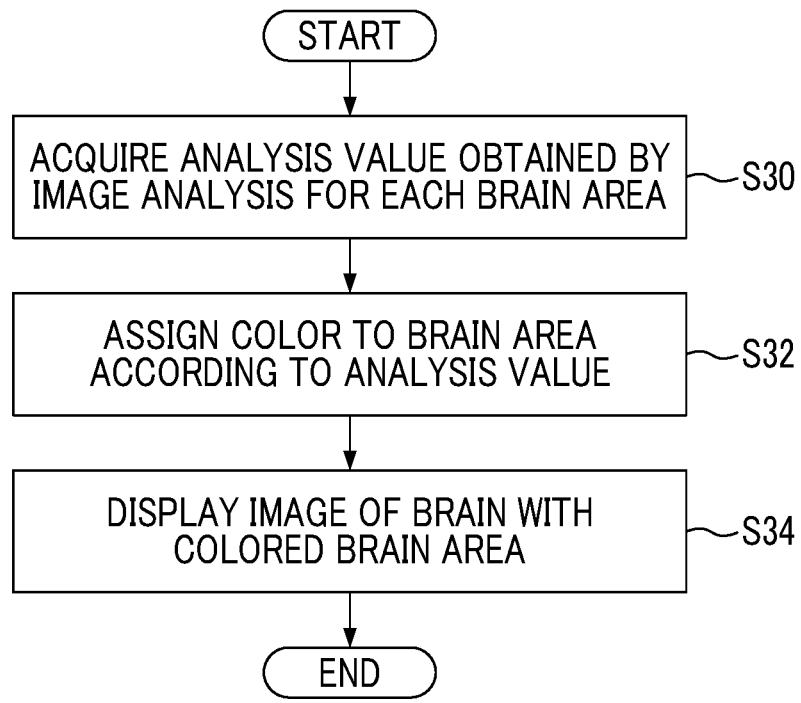
FIG. 26 is a flowchart relating to a display of an analysis result.

FIG. 26 is a flowchart relating to a display of an analysis result.

As shown in FIG. 26, first, the display controller 12F acquires an analysis value obtained by image analysis for each brain area (step S30). Next, the display controller 12F assigns a color to the brain area according to the analysis value (step S32), and causes the monitor 24 to display an image in which a color according to the analysis value is added to the brain area (step S34).

The display controller 12F sets a brain area having the largest volume change amount, volume decrease amount, or shape change amount to red, and designate a color of the brain area by a color scale that sequentially changes to orange, yellow, yellow-green, green, blue, and dark blue as these values become smaller. The display controller 12F sets a brain area having a relatively large evaluation value (size) of infarction or bleeding to red, and designate a color of the brain area by a color scale that sequentially changes to orange, yellow, yellow-green, green, blue, and dark blue as these values become smaller. As a result, it is possible to highlight a brain area having a large shape change or a brain area having a high evaluation value of a lesion and a relatively high importance in brain diagnosis.

In the present embodiment, a color according to an analysis value is added to a brain area, but the present invention is not limited to this. For example, an analysis value may be displayed by changing a brightness or a transparency of an image.

In addition, the type of analysis value to be displayed by a color or the like may be switched by providing a menu for selecting the type of analysis value.

Figure 27:
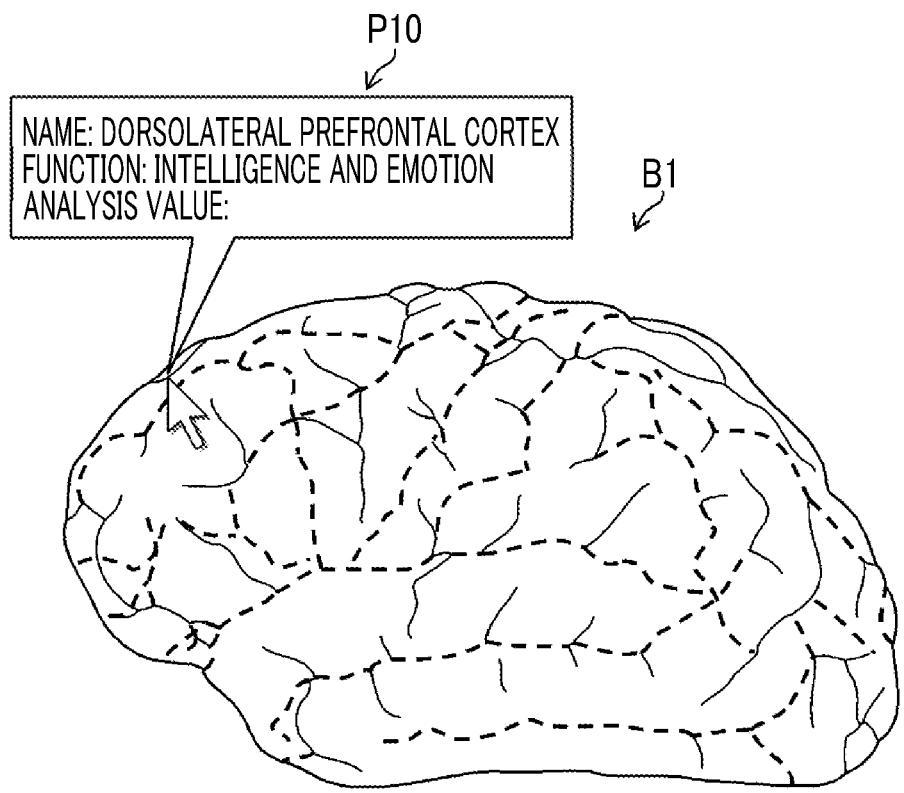
FIG. 27 is a diagram showing an example (a three-dimensional display) of a display of the brain image.

FIG. 27 is a diagram showing an example (a three-dimensional display) of a display of the brain image.

The three-dimensional brain image B1 shown in FIG. 27 is a volume rendering (VR) image in which the brain is divided into brain areas and displayed three-dimensionally. In FIG. 27, the boundaries of the brain area are indicated by broken lines. An operator can perform operations of enlargement and reduction of a display, rotation, and orientation change of the brain by the operation unit 22.

As shown in FIG. 27, in a case where a cursor is moved by the mouse of the operation unit 22 and a position in the three-dimensional brain image B1 is designated (clicked), coordinates of the designated voxel are specified. The information processing unit 12E specifies the brain area presenting at a position of the specified voxel, and acquires a position and an extent thereof from the analysis result table T10. Then, the display controller 12F highlights the specified brain area by increasing or maximizing a transmittance of a brain area other than the specified brain area. The name, function, and analysis value of the specified brain area may be acquired from the analysis result table T10 and displayed on a pop-up display P10.

Figure 28:
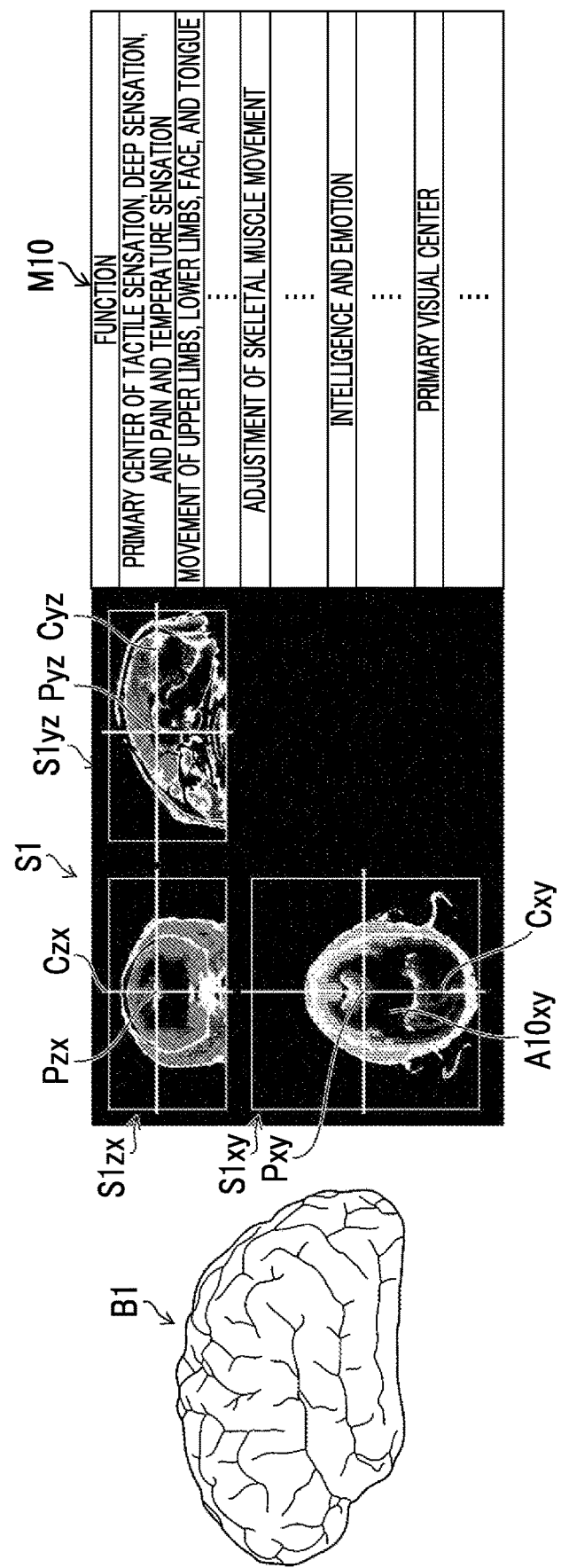
FIG. 28 is a diagram showing another example (a parallel display) of a display of the brain image.

FIG. 28 is a diagram showing another example (a parallel display) of a display of the brain image.

In the example shown in FIG. 28, the three-dimensional brain image B1 and an orthogonal three cross-sectional image S1 are displayed in parallel.

The three-dimensional brain image B1 may be displayed by changing a color, a brightness, and a transparency of the brain area according to the analysis value. In addition, in the three-dimensional brain image B1, a color or a thickness of an outline of the brain area may be changed according to the analysis value. In the three-dimensional brain image B1, a display according to the analysis value and a display of an MRI image such as a T1WI may be switched.

In a display region of the orthogonal three cross-sectional image S1, a zx cross-sectional image S1zx, a yz cross-sectional image S1yz, and an xy cross-sectional image S1xy of the brain are displayed side by side. The zx cross-sectional image S1zx, the yz cross-sectional image S1yz, and the xy cross-sectional image S1xy may be displayed by changing a color, a brightness, and a transparency of the brain area according to the analysis value. In addition, in the zx cross-sectional image S1zx, the yz cross-sectional image S1yz, and the xy cross-sectional image S1xy, a color or a thickness of an outline of the brain area may be changed according to the analysis value. In the zx cross-sectional image S1zx, the yz cross-sectional image S1yz, and the xy cross-sectional image S1xy, a display according to the analysis value and a display of an MRI image such as a T1WI may be switched.

An operator moves any of reference points Pzx, Pyz, and Pzy in the zx cross-sectional image S1zx, the yz cross-sectional image S1yz, and the xy cross-sectional image S1xy by a mouse to move a reference point of the orthogonal three cross-sectional image, thereby displaying a desired cross-section of the brain on the monitor 24. Cross lines Czx, Cyz, and Czy in the figure move in conjunction with the movements of Pzx, Pyz, and Pzy, respectively, and indicate a position of the cross-sectional image being displayed.

In the three-dimensional brain image B1 or the orthogonal three cross-sectional image S1, in a case where a position in the three-dimensional brain image B1 or the orthogonal three cross-sectional image S1 is designated (clicked), coordinates of the designated voxel are specified. The information processing unit 12E specifies the brain area presenting at a position of the specified voxel, and acquires a position and an extent thereof from the analysis result table T10. Therefore, the display controller 12F increases or maximizes a transmittance of a brain area other than the brain area specified in the three-dimensional brain image B1, and also decreases or minimizes a brightness of a brain area other than the brain area specified in the orthogonal three cross-sectional image S1 (making it the same color as a background color or filling it in black), and thus highlights the specified brain area.

Figure 29:
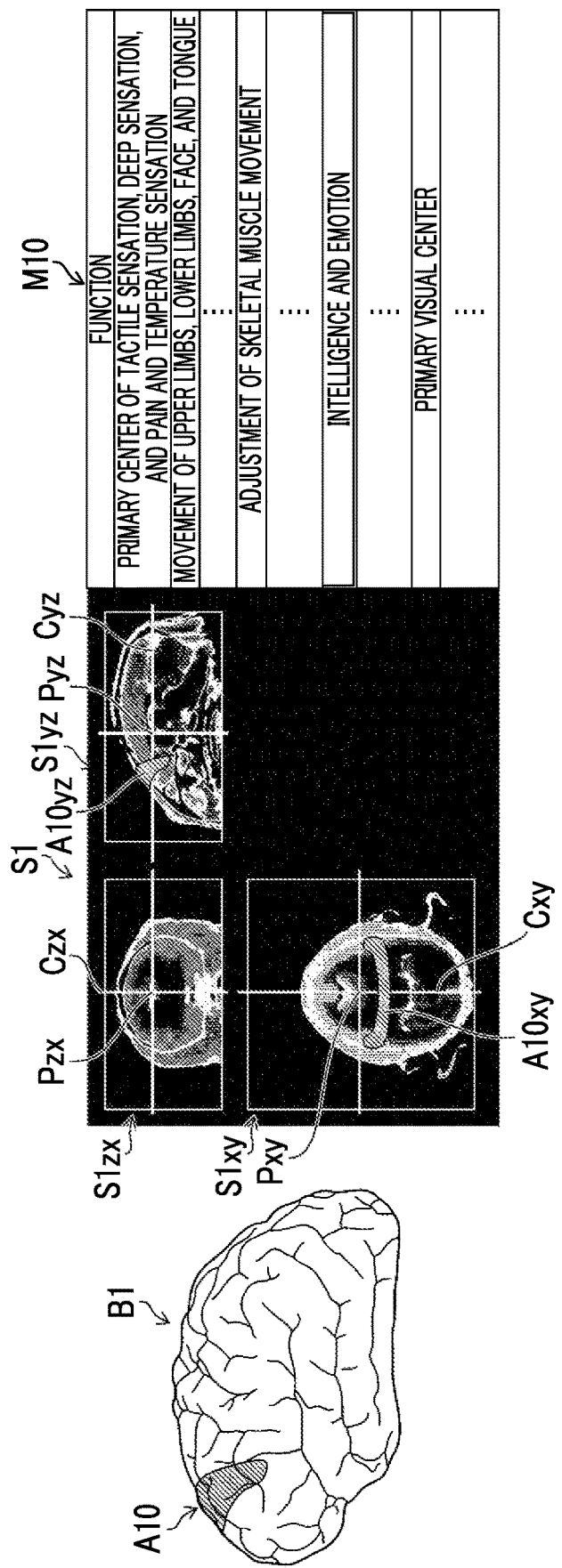
FIG. 29 is a diagram showing highlighting of the brain area in another example (a parallel display) of a display of the brain image.

In the example shown in FIG. 28, a menu M10 is displayed next to the orthogonal three cross-sectional image S1. The menu M10 includes a brain function button indicating a function of the brain. In a case where an operator selects the brain function button from the menu M10 using the operation unit 22, the display controller 12F highlights the brain area A10 corresponding to the selected brain function button as shown in FIG. 29. In the yz cross-sectional image S1yz and the xy cross-sectional image S1xy, the brain area A10 is displayed as the cross-sectional images A10yz and Al0xy of the brain area, respectively. In the example shown in FIG. 29, only one brain area corresponding to the selected function is shown, but in a case where there are a plurality of brain areas corresponding to the selected function, all the brain areas may be highlighted.

In the present embodiment, when a brain area is selected, another brain area corresponding to the same function as the selected brain area may not be displayed. In this case, after receiving an instruction of end of diagnosis and check of the selected brain area, an image of another brain area corresponding to the same function as the selected brain area may be displayed. In addition, in a case of displaying an image of another brain area corresponding to the same function as the selected brain area, the brain area may be selected and displayed according to the relevance (correlation value) between the function and the brain area.

The brain area may be selected and displayed according to the relevance (correlation value) between the function selected from the menu M10 and the brain area. For example, only the brain area where the relevance between the function selected from the menu M10 and the brain area is the maximum may be displayed, or the brain area whose relevance is equal to or higher than a threshold value or whose relevance ranking is up to the n-th order from the highest priority may be selected and displayed.

In the menu M10, a color, a brightness, or a transparency of the brain function button may be changed according to the analysis value. For example, in a case where a part or the whole of the brain area related to a language function atrophies as compared with the past patient image, a button related to the language function may be colored red.

In the present embodiment, the display controller 12F may create three-dimensional data using the analysis value calculated for each brain area as a voxel value, and create the three-dimensional brain image B1 using the three-dimensional data.

For each brain function, the display controller 12F may store the analysis value as a voxel value for the voxel of the brain area corresponding to the same function, and create three-dimensional data in which a voxel value other than the brain area corresponding to the same function is set to a predetermined value, for example, −9999. Therefore, the display controller 12F may perform color coding for each brain area by a color scale according to the analysis value stored as a voxel value, and make the voxel having a voxel value of −9999 lighter in color, lower in brightness, or transparent, for example. In this manner, the display controller 12F can create the three-dimensional brain image B1 and the orthogonal three cross-sectional image S1 for selectively displaying the brain area corresponding to each function. In this case, for example, it is possible to display the brain area corresponding to each function such as "memory", "language", or "hearing", reflecting the analysis value.

In a case of selecting and displaying the brain area for each function, a brain area other than the brain area selected as an object to be displayed may not be displayed at all, or a certain area around the brain area selected as an object to be displayed may be displayed. In this case, for example, in the three-dimensional brain image B1 and the orthogonal three cross-sectional image S1, display may be performed for a surrounding region having a maximum size of about 10% of the brain area selected as an object to be displayed. In addition, the surrounding region may be made lighter in color, lower in brightness, or transparent as the distance from the brain area selected as an object to be displayed increases. This makes it possible to check a situation around the brain area selected as an object to be displayed.

In the three-dimensional brain image B1 or the orthogonal three cross-sectional image S1, a cursor is moved by the mouse of the operation unit 22 and a brain area in the image is selected, and thus the name, function, and analysis value of the brain area may be displayed on the pop-up display P10.

Figure 30:
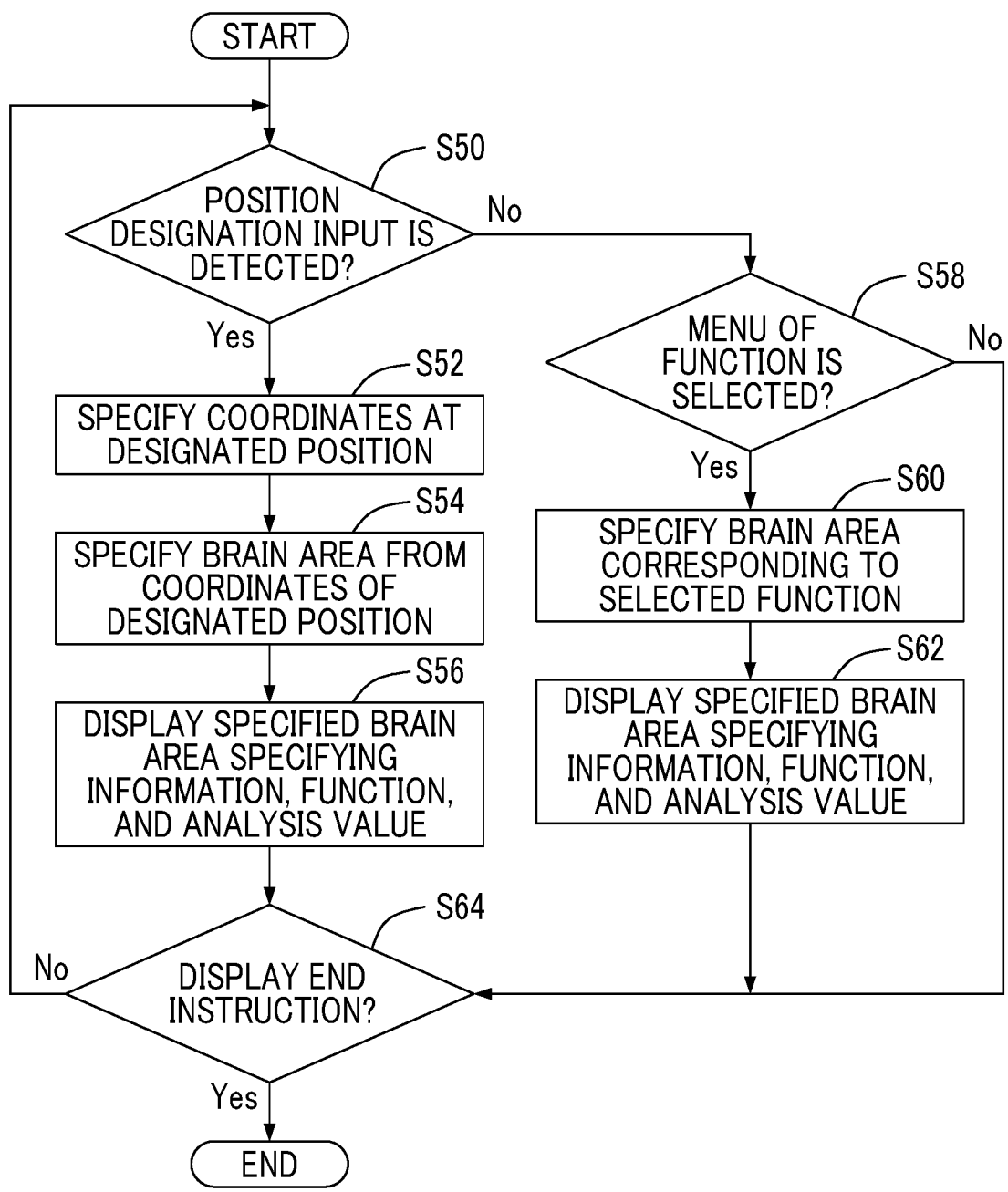
FIG. 30 is a flowchart relating to display control in a parallel display.

FIG. 30 is a flowchart relating to display control in a parallel display.

In the example shown in FIG. 30, first, in the VR image B1 or the orthogonal three cross-sectional image S1, the information processing unit 12E determines whether or not a predetermined position is designated (clicked) by the mouse operation of the operation unit 22 (step S50). In a case where a position designation input is detected (Yes in step S50), the information processing unit 12E specifies coordinates on the monitor 24 at the designated position (step S52). Next, the information processing unit 12E specifies the brain area corresponding to the coordinates of the designated position (step S54), and the display controller 12F displays the name, function, and analysis value of the brain area on the monitor 24 (step S56).

On the other hand, in a case where the operation unit 22 selects a brain function in the menu M10 related to a function (No in step S50 and Yes in step S58), the information processing unit 12E specifies the brain area corresponding to the selected function (step S60), and the display controller 12F displays the name, function and analysis value of the brain area on the monitor 24 (step S62).

Display of the name, function, and analysis value of the brain area in steps S56 and S62 may be displayed in a pop-up for each brain area, or may be displayed on a table together with the brain area specifying information. In a case where the brain area specifying information or the like is displayed in a table, the corresponding brain area may be highlighted in the three-dimensional brain image B1 and the orthogonal three cross-sectional image S1 in a case of selecting the brain area specifying information of the table.

Then, in a case where the operation unit 22 inputs a display end instruction (Yes in step S64), the display of the brain image is ended.

According to the present embodiment, information on another brain area having the same function as the brain area focused on as a diagnosis target can be displayed on the monitor 24 at the same time. In this manner, the analysis value of the brain area responsible for the same function can be checked at a glance. For example, since the atrophy rate of the brain area corresponding to the same function as the focused brain area can be displayed as an analysis value, diagnosis of dementia using a brain image is facilitated.

The present embodiment is not limited to the medical information display apparatus 1, and can be realized as a medical information display method for causing the medical information display apparatus 1 to perform each step of display control according to the present embodiment, a medical information display program for causing a computer to execute each function of display control according to the present embodiment, and a non-transitory recording medium that stores the medical information display program.

In the above present embodiment, for example, the hardware structures of processing units for executing various kinds of processing, (such as the image acquisition unit 12A, the data acquisition unit 12B, the brain area division unit 12C, the image analysis unit 12D, the information processing unit 12E, and the display controller 12F), are various processors shown below. The various processors include a central processing unit (CPU) that is a general-purpose processor that executes software (program) to function as various processing units, a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of these various processors, or may be configured by two or more processors of the same type or different types (for example, a plurality of FPGAs or a combination of a CPU and an FPGA). Alternatively, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

In addition, the hardware structure of these various processors is an electrical circuit (circuitry) in the form of a combination of circuit elements, such as semiconductor elements.

EXPLANATION OF REFERENCES

1: medical information display apparatus
2: PACS
3: electronic medical record
4: MRI apparatus
10: computer
12: CPU
14: main memory
16: storage
18: optical disc drive
20: communication interface
22: operation unit (mouse and keyboard)
24: monitor
3012A: image acquisition unit
12A: image acquisition unit
12B: data acquisition unit
12C: brain area division unit
12D: image analysis unit
12E: information processing unit
12F: display controller
S10 to S24, S30 to S34, S50 to S64: each step of display control

What is claimed is:

1. A medical information display apparatus, comprising:
a storage medium;
a display; and
a processor, coupled to the storage medium and the display, wherein the processor is configured to function as:
an image acquisition unit that acquires a first brain image which is a brain image of a subject captured at a first time point and a second brain image which is a brain image of the subject captured at a second time point later in time than the first time point;
a registration unit that performs registration between the first brain image and the second brain image;
an image analysis unit that extracts a first cavity region and a second cavity region from the first brain image and the second brain image, respectively;
a display controller that displays, on the display, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image; and a brain area division unit that divides at least one of the first brain image or the second brain image into a plurality of brain areas.

2. The medical information display apparatus according to claim 1, wherein the display controller displays, on the display, a cavity contraction part included in the first cavity region in the first brain image and included in a second non-cavity region which is a region other than the second cavity region in the second brain image in a distinguishable manner from a region other than the cavity contraction part.

3. A medical information display apparatus, comprising:

a storage medium;

a display; and a processor, coupled to the storage medium and the display, wherein the processor is configured to function as:

an image acquisition unit that acquires a first brain image which is a brain image of a subject captured at a first time point and a second brain image which is a brain image of the subject captured at a second time point later in time than the first time point;

a registration unit that performs registration between the first brain image and the second brain image;

an image analysis unit that extracts a first cavity region and a second cavity region from the first brain image and the second brain image, respectively;

a display controller that displays, on the display, a cavity contraction part included in the first cavity region in the first brain image and included in a second non-cavity region which is a region other than the second cavity region in the second brain image in a distinguishable manner from a region other than the cavity contraction part from a result of the registration between the first brain image and the second brain image; and a brain area division unit that divides at least one of the first brain image or the second brain image into a plurality of brain areas.

4. The medical information display apparatus according to claim 1, wherein the display controller displays, on the display, a cavity part that is a region commonly included in both the first cavity region and the second cavity region in a distinguishable manner from a region other than the cavity part.

5. The medical information display apparatus according to claim 2, wherein the display controller displays, on the display, a cavity part that is a region commonly included in both the first cavity region and the second cavity region in a distinguishable manner from a region other than the cavity part.

6. The medical information display apparatus according to claim 1, wherein the display controller displays, on the display, a non-cavity part that is a region commonly included in both the first non-cavity region which is a region other than the first cavity region in the first brain image and a second non-cavity region which is a region other than the second cavity region in the second brain image in a distinguishable manner from a region other than the non-cavity part.

7. The medical information display apparatus according to claim 2, wherein the display controller displays, on the display, a non-cavity part that is a region commonly included in both the first non-cavity region which is a region other than the first cavity region in the first brain image and a second non-cavity region which is a region other than the second cavity region in the second brain image in a distinguishable manner from a region other than the non-cavity part.

8. The medical information display apparatus according to claim 1, wherein the image analysis unit calculates a change of each brain area due to a change of the cavity region in the first brain image and the second brain image, and the display controller displays the change of each brain area on the display.

9. The medical information display apparatus according to claim 2, wherein the image analysis unit calculates a change of each brain area due to a change of the cavity region in the first brain image and the second brain image, and the display controller displays the change of each brain area on the display.

10. The medical information display apparatus according to claim 8, wherein the image analysis unit calculates at least one of a size change or a shape change of each brain area due to the change of the cavity region in the first brain image and the second brain image.

11. The medical information display apparatus according to claim 9, wherein the image analysis unit calculates at least one of a size change or a shape change of each brain area due to the change of the cavity region in the first brain image and the second brain image.

12. The medical information display apparatus according to claim 8, wherein the processor is further configured to function as:

a first data acquisition unit that acquires information indicating correspondence between the brain area and a brain function, wherein the display controller displays information on the brain function corresponding to each brain area on the display.

13. The medical information display apparatus according to claim 1, wherein the image analysis unit calculates a change of each brain area due to a change of the cavity region in the first brain image and the second brain image, and the display controller displays the change of each brain area on the display, wherein the processor is further configured to function as:

a first data acquisition unit that acquires information indicating correspondence between the brain area and a brain function, wherein the display controller displays information on the brain function corresponding to each brain area on the display.

14. The medical information display apparatus according to claim 8, wherein the processor is further configured to function as:

a second data acquisition unit that acquires a table showing relevance between at least one item included in clinical diagnostic information on dementia and the brain area, wherein the display controller specifies at least one item included in the clinical diagnostic information corresponding to each brain area and displays the specified item on the display based on the table.

15. The medical information display apparatus according to claim 10, wherein the processor is further configured to function as:

a second data acquisition unit that acquires a table showing relevance between at least one item included in clinical diagnostic information on dementia and the brain area, wherein the display controller specifies at least one item included in the clinical diagnostic information corresponding to each brain area and displays the specified item on the display based on the table.

16. A medical information display method, comprising:

an image acquisition step of acquiring a first brain image which is a brain image of a subject captured at a first time point and a second brain image which is a brain image of the subject captured at a second time point later in time than the first time point;

a registration step of performing registration between the first brain image and the second brain image;

an image analysis step of extracting a first cavity region and a second cavity region from the first brain image and the second brain image, respectively;

a display control step of displaying, on a display, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image; and a brain area division step of dividing at least one of the first brain image or the second brain image into a plurality of brain areas.

17. A medical information display method, comprising:

an image acquisition step of acquiring a first brain image which is a brain image of a subject captured at a first time point and a second brain image which is a brain image of the subject captured at a second time point later in time than the first time point;

a registration step of performing registration between the first brain image and the second brain image;

an image analysis step of extracting a first cavity region and a second cavity region from the first brain image and the second brain image, respectively;

a display control step of displaying, on a display, a cavity contraction part included in the first cavity region in the first brain image and included in a second non-cavity region which is a region other than the second cavity region in the second brain image in a distinguishable manner from a region other than the cavity contraction part from a result of the registration between the first brain image and the second brain image; and a brain area division step of dividing at least one of the first brain image or the second brain image into a plurality of brain areas.

18. A non-transitory computer readable recording medium storing a medical information display program for causing a computer to realize:

an image acquisition function of acquiring a first brain image which is a brain image of a subject captured at a first time point and a second brain image which is a brain image of the subject captured at a second time point later in time than the first time point;

a registration function of performing registration between the first brain image and the second brain image;

an image analysis function of extracting a first cavity region and a second cavity region from the first brain image and the second brain image, respectively;

a display control function of displaying, on a display, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image; and a brain area division function of dividing at least one of the first brain image or the second brain image into a plurality of brain areas.

19. A non-transitory computer readable recording medium storing a medical information display program for causing a computer to realize:

an image acquisition function of acquiring a first brain image which is a brain image of a subject captured at a first time point and a second brain image which is a brain image of the subject captured at a second time point later in time than the first time point;

a registration function of performing registration between the first brain image and the second brain image;

an image analysis function of extracting a first cavity region and a second cavity region from the first brain image and the second brain image, respectively;

a display control function of displaying, on a display, a cavity contraction part included in the first cavity region in the first brain image and included in a second non-cavity region which is a region other than the second cavity region in the second brain image in a distinguishable manner from a region other than the cavity contraction part from a result of the registration between the first brain image and the second brain image; and a brain area division function of dividing at least one of the first brain image or the second brain image into a plurality of brain areas.

20. A medical information display apparatus according to another aspect of the present invention comprises:

a memory for storing an instruction for causing a computer to execute processing; and a processor configured to execute the stored instruction, in which the processor acquires a first brain image which is a brain image of a subject captured at a first time point and a second brain image which is a brain image of the subject captured at a second time point later in time than the first time point, performs registration between the first brain image and the second brain image, extracts a first cavity region and a second cavity region from the first brain image and the second brain image, respectively, displays, on the display, a cavity expansion part included in a first non-cavity region, which is a region other than the first cavity region in the first brain image, and included in the second cavity region in the second brain image in a distinguishable manner from a region other than the cavity expansion part from a result of the registration between the first brain image and the second brain image, and divides at least one of the first brain image or the second brain image into a plurality of brain areas.

\* \* \* \* \*